US009355273B2

(12) United States Patent
Stevens et al.

(10) Patent No.: US 9,355,273 B2
(45) Date of Patent: May 31, 2016

(54) SYSTEM AND METHOD FOR THE PROTECTION AND DE-IDENTIFICATION OF HEALTH CARE DATA

(75) Inventors: Steven E. Stevens, Chalfont, PA (US); Andrew E. Kress, Gladwyne, PA (US); Adam Dublin, Yardley, PA (US)

(73) Assignee: BANK OF AMERICA, N.A., AS COLLATERAL AGENT, New York, NY (US)

( * ) Notice: Subject to any disclaimer, the term of this patent is extended or adjusted under 35 U.S.C. 154(b) by 1305 days.

(21) Appl. No.: 11/945,795

(22) Filed: Nov. 27, 2007

(65) Prior Publication Data

US 2008/0147554 A1    Jun. 19, 2008

Related U.S. Application Data

(60) Provisional application No. 60/875,392, filed on Dec. 18, 2006.

(51) Int. Cl.
| | |
|---|---|
| *G06F 21/00* | (2013.01) |
| *G06F 21/62* | (2013.01) |
| *G06F 19/00* | (2011.01) |
| *H04L 29/06* | (2006.01) |

(52) U.S. Cl.
CPC .......... *G06F 21/6254* (2013.01); *G06F 19/322* (2013.01); *G06F 2221/2107* (2013.01); *H04L 63/0428* (2013.01)

(58) Field of Classification Search
USPC .......................................................... 705/50
See application file for complete search history.

(56) References Cited

U.S. PATENT DOCUMENTS

| | | | |
|---|---|---|---|
| 3,752,904 | A | 8/1973 | Waterbury |
| 3,896,266 | A | 7/1975 | Waterbury |
| 4,823,265 | A | 4/1989 | Nelson |
| 4,979,832 | A | 12/1990 | Ritter |
| 4,992,940 | A | 2/1991 | Dworkin |
| 4,993,068 | A | 2/1991 | Piosenka et al. |
| 5,003,539 | A | 3/1991 | Takemoto et al. |
| 5,005,200 | A | 4/1991 | Fischer |
| 5,060,263 | A | 10/1991 | Bosen |
| 5,070,452 | A | 12/1991 | Doyle, Jr. et al. |

(Continued)

FOREIGN PATENT DOCUMENTS

| | | |
|---|---|---|
| EP | 0732014 B1 | 9/1994 |
| EP | 0770967 A2 | 5/1997 |

(Continued)

OTHER PUBLICATIONS

Scheuren et al., "HIPAA Certification for SDI's De-Identification Technology" Washington D.C. Jun. 4, 2007; pp. 1-24.

(Continued)

*Primary Examiner* — Dante Ravetti
(74) *Attorney, Agent, or Firm* — Fish & Richardson P.C.

(57) ABSTRACT

A system for protecting and de-identifying healthcare data includes a storage device for storing the healthcare data and personally identifiable information for a person and a processor in communication with the database. The processor generates an anonymous linking code using a keyed hash function and a second hash function. The anonymous linking code is based at least in part on a portion of the personally identifiable information. The processor further appends the anonymous linking code to the healthcare data for the person.

14 Claims, 5 Drawing Sheets

(56) References Cited

U.S. PATENT DOCUMENTS

| | | | |
|---|---|---|---|
| 5,084,828 A | 1/1992 | Kaufman et al. |
| 5,175,681 A | 12/1992 | Iwai et al. |
| 5,202,982 A | 4/1993 | Gramlich et al. |
| 5,214,702 A | 5/1993 | Fischer |
| 5,257,369 A | 10/1993 | Skeen et al. |
| 5,265,247 A | 11/1993 | Wienck et al. |
| 5,285,494 A | 2/1994 | Sprecher et al. |
| 5,293,615 A | 3/1994 | Amada |
| 5,295,261 A | 3/1994 | Simonetti |
| 5,297,202 A | 3/1994 | Kapp et al. |
| 5,299,121 A | 3/1994 | Brill et al. |
| 5,301,105 A | 4/1994 | Cummings, Jr. |
| 5,325,290 A | 6/1994 | Cauffman et al. |
| 5,331,544 A | 7/1994 | Lu et al. |
| 5,365,589 A | 11/1994 | Gutowitz |
| 5,371,797 A | 12/1994 | Bocinsky, Jr. |
| 5,403,639 A | 4/1995 | Belsan et al. |
| 5,410,602 A | 4/1995 | Finkelstein et al. |
| 5,420,786 A | 5/1995 | Felthauser et al. |
| 5,444,823 A | 8/1995 | Nguyen |
| 5,454,101 A | 9/1995 | Mackay et al. |
| 5,471,382 A | 11/1995 | Tallman et al. |
| 5,490,060 A | 2/1996 | Malec et al. |
| 5,497,486 A | 3/1996 | Stolfo et al. |
| 5,499,293 A | 3/1996 | Behram et al. |
| 5,502,764 A | 3/1996 | Naccache |
| 5,519,607 A | 5/1996 | Tawil |
| 5,526,257 A | 6/1996 | Lerner |
| 5,557,518 A | 9/1996 | Rosen |
| 5,557,780 A | 9/1996 | Edwards et al. |
| 5,560,006 A | 9/1996 | Layden et al. |
| 5,581,749 A | 12/1996 | Hossain et al. |
| 5,606,610 A | 2/1997 | Johansson |
| 5,615,264 A | 3/1997 | Kazmierczak et al. |
| 5,634,016 A | 5/1997 | Steadham, Jr. et al. |
| 5,644,778 A | 7/1997 | Burks et al. |
| 5,652,842 A | 7/1997 | Siegrist, Jr. et al. |
| 5,664,109 A | 9/1997 | Johnson et al. |
| 5,666,492 A | 9/1997 | Rhodes et al. |
| 5,680,611 A | 10/1997 | Rail et al. |
| 5,699,428 A | 12/1997 | McDonnal et al. |
| 5,704,044 A | 12/1997 | Tarter et al. |
| 5,708,828 A | 1/1998 | Coleman |
| 5,719,938 A | 2/1998 | Haas et al. |
| 5,721,777 A | 2/1998 | Blaze |
| 5,724,575 A | 3/1998 | Hoover et al. |
| 5,734,838 A | 3/1998 | Robinson et al. |
| 5,737,539 A | 4/1998 | Edelson et al. |
| 5,745,899 A | 4/1998 | Burrows |
| 5,748,765 A | 5/1998 | Takhar |
| 5,754,938 A | 5/1998 | Herz et al. |
| 5,758,085 A | 5/1998 | Kouoheris et al. |
| 5,758,095 A | 5/1998 | Albaum et al. |
| 5,758,147 A | 5/1998 | Chen et al. |
| 5,758,355 A | 5/1998 | Buchanan |
| 5,761,500 A | 6/1998 | Gallant et al. |
| 5,781,893 A | 7/1998 | Felthauser et al. |
| 5,784,565 A | 7/1998 | Lewine |
| 5,787,186 A | 7/1998 | Schroeder |
| 5,787,435 A | 7/1998 | Burrows |
| 5,793,969 A | 8/1998 | Kamentsky et al. |
| 5,794,246 A | 8/1998 | Sankaran et al. |
| 5,799,086 A | 8/1998 | Sudia |
| 5,799,308 A | 8/1998 | Dixon |
| 5,806,074 A | 9/1998 | Souder et al. |
| 5,809,494 A | 9/1998 | Nguyen |
| 5,818,836 A | 10/1998 | DuVal |
| 5,821,871 A | 10/1998 | Benzler |
| 5,823,948 A | 10/1998 | Ross, Jr. et al. |
| 5,825,906 A | 10/1998 | Obata et al. |
| 5,832,449 A | 11/1998 | Cunningham |
| 5,832,494 A | 11/1998 | Egger et al. |
| 5,845,255 A | 12/1998 | Mayaud |
| 5,845,284 A | 12/1998 | Robinson |
| 5,848,373 A | 12/1998 | DeLorme et al. |
| 5,852,822 A | 12/1998 | Srinivasan et al. |
| 5,867,821 A | 2/1999 | Ballantyne et al. |
| 5,870,770 A | 2/1999 | Wolfe |
| 5,876,926 A | 3/1999 | Beecham |
| 5,890,129 A | 3/1999 | Spurgeon |
| 5,890,156 A | 3/1999 | Rekieta et al. |
| 5,897,641 A | 4/1999 | Ruddy et al. |
| 5,897,989 A | 4/1999 | Beecham |
| 5,907,677 A | 5/1999 | Glenn et al. |
| 5,911,132 A | 6/1999 | Sloane |
| 5,915,209 A | 6/1999 | Lawrence |
| 5,915,240 A | 6/1999 | Karpf |
| 5,918,208 A | 6/1999 | Javitt |
| 5,920,854 A | 7/1999 | Kirsch et al. |
| 5,923,754 A | 7/1999 | Angelo et al. |
| 5,926,810 A | 7/1999 | Noble et al. |
| 5,937,063 A | 8/1999 | Davis |
| 5,940,507 A | 8/1999 | Cane et al. |
| 5,940,835 A | 8/1999 | Sit |
| 5,956,400 A | 9/1999 | Chaum et al. |
| 5,956,716 A | 9/1999 | Kenner et al. |
| 5,961,593 A | 10/1999 | Gabber et al. |
| 5,966,695 A | 10/1999 | Melchione et al. |
| 5,970,462 A | 10/1999 | Reichert |
| 5,970,492 A | 10/1999 | Nielsen |
| 5,978,791 A | 11/1999 | Farber et al. |
| 5,987,448 A | 11/1999 | Evans et al. |
| 5,987,464 A | 11/1999 | Schneider |
| 5,987,572 A | 11/1999 | Weidner |
| 5,991,731 A | 11/1999 | Colon et al. |
| 5,991,751 A | 11/1999 | Rivette et al. |
| 5,991,758 A | 11/1999 | Ellard |
| 5,991,765 A | 11/1999 | Vethe |
| 5,995,939 A | 11/1999 | Berman et al. |
| 5,999,908 A | 12/1999 | Abelow |
| 6,003,006 A | 12/1999 | Colella et al. |
| 6,012,051 A | 1/2000 | Sammon, Jr. et al. |
| 6,014,631 A | 1/2000 | Teagarden et al. |
| 6,018,713 A | 1/2000 | Coli et al. |
| 6,021,200 A | 2/2000 | Fischer |
| 6,024,287 A | 2/2000 | Takai et al. |
| 6,035,306 A | 3/2000 | Lowenthal et al. |
| 6,061,658 A | 5/2000 | Chou et al. |
| 6,073,140 A | 6/2000 | Morgan et al. |
| 6,078,924 A | 6/2000 | Ainsbury et al. |
| 6,079,021 A | 6/2000 | Abadi et al. |
| 6,085,322 A | 7/2000 | Romney et al. |
| 6,088,717 A | 7/2000 | Reed et al. |
| 6,101,749 A | 8/2000 | Inbar et al. |
| 6,195,643 B1 | 2/2001 | Maxwell |
| 6,195,661 B1 | 2/2001 | Filepp et al. |
| 6,226,675 B1 | 5/2001 | Meltzer et al. |
| 6,249,768 B1 | 6/2001 | Tulskie, Jr. et al. |
| 6,249,769 B1 | 6/2001 | Ruffin et al. |
| 6,253,203 B1 | 6/2001 | O'Flaherty et al. |
| 6,266,675 B1 | 7/2001 | Evans et al. |
| 6,285,983 B1 | 9/2001 | Jenkins |
| 6,289,111 B1 | 9/2001 | Takhar |
| 6,295,608 B1 | 9/2001 | Parkes et al. |
| 6,302,844 B1 | 10/2001 | Walker et al. |
| 6,317,700 B1 | 11/2001 | Bagne |
| 6,317,834 B1 | 11/2001 | Gennaro et al. |
| 6,321,201 B1 | 11/2001 | Dahl |
| 6,321,205 B1 | 11/2001 | Eder |
| 6,330,976 B1 | 12/2001 | Dymetman et al. |
| 6,336,114 B1 | 1/2002 | Garrison |
| 6,341,267 B1 | 1/2002 | Taub |
| 6,360,324 B2 | 3/2002 | Van Blarkom |
| 6,363,525 B1 | 3/2002 | Dougherty et al. |
| 6,397,224 B1 * | 5/2002 | Zubeldia ............... G06F 19/322 |
| 6,408,263 B1 | 6/2002 | Summers |
| 6,415,280 B1 | 7/2002 | Farber et al. |
| 6,421,650 B1 | 7/2002 | Goetz et al. |
| 6,430,292 B1 | 8/2002 | Ito et al. |
| 6,434,533 B1 | 8/2002 | Fitzgerald |
| 6,449,621 B1 | 9/2002 | Pettovello |
| 6,473,609 B1 | 10/2002 | Schwartz et al. |
| 6,496,931 B1 | 12/2002 | Rajchel et al. |
| 6,523,027 B1 | 2/2003 | Underwood |

(56) References Cited

U.S. PATENT DOCUMENTS

| | | | |
|---|---|---|---|
| 6,523,041 B1 | 2/2003 | Morgan et al. |
| 6,584,472 B2 | 6/2003 | Classen |
| 6,654,721 B2 | 11/2003 | Handelman |
| 6,654,724 B1 | 11/2003 | Rubin et al. |
| 6,704,739 B2 | 3/2004 | Craft et al. |
| 6,704,740 B1 | 3/2004 | Lang |
| 6,704,873 B1 | 3/2004 | Underwood |
| 6,708,156 B1 | 3/2004 | Von Gonten |
| 6,732,113 B1 | 5/2004 | Ober et al. |
| 6,734,886 B1 | 5/2004 | Hagan et al. |
| 6,735,399 B2 | 5/2004 | Tabb et al. |
| 6,782,370 B1 | 8/2004 | Stack |
| 6,792,412 B1 | 9/2004 | Sullivan et al. |
| 6,873,979 B2 | 3/2005 | Fishman et al. |
| 6,874,085 B1 | 3/2005 | Koo et al. |
| 6,915,265 B1 | 7/2005 | Johnson |
| 6,934,687 B1 | 8/2005 | Papierniak et al. |
| 6,938,022 B1 | 8/2005 | Singhal |
| 6,988,075 B1 | 1/2006 | Hacker |
| 7,016,882 B2 | 3/2006 | Afeyan et al. |
| 7,092,896 B2 | 8/2006 | Delurgio et al. |
| 7,127,432 B2 | 10/2006 | Rubin et al. |
| 7,143,289 B2 | 11/2006 | Denning et al. |
| 7,184,947 B2 | 2/2007 | Matsuoka et al. |
| 7,200,578 B2 | 4/2007 | Paltenghe et al. |
| 7,309,001 B2 | 12/2007 | Banfield et al. |
| 7,346,521 B2 | 3/2008 | Tolle et al. |
| 7,376,677 B2 | 5/2008 | Ober et al. |
| 7,386,526 B1 | 6/2008 | Chappel |
| 7,428,706 B2 | 9/2008 | Hagan et al. |
| 7,668,820 B2 | 2/2010 | Zuleba |
| 7,865,376 B2 | 1/2011 | Ober et al. |
| 7,885,882 B1 | 2/2011 | Brander et al. |
| 8,275,850 B2 | 9/2012 | Kohan et al. |
| 8,473,452 B1 | 6/2013 | Ober et al. |
| 8,930,404 B2 | 1/2015 | Ober et al. |
| 2001/0011247 A1 | 8/2001 | O'Flaherty et al. |
| 2001/0019614 A1 | 9/2001 | Madoukh |
| 2001/0027331 A1 | 10/2001 | Thompson |
| 2001/0047281 A1 | 11/2001 | Keresman, III et al. |
| 2002/0004900 A1 | 1/2002 | Patel |
| 2002/0073099 A1 | 6/2002 | Gilbert et al. |
| 2002/0073138 A1 | 6/2002 | Gilbert et al. |
| 2002/0080968 A1 | 6/2002 | Olsson |
| 2002/0083192 A1 | 6/2002 | Alisuag |
| 2002/0116615 A1 | 8/2002 | Nguyen et al. |
| 2002/0128860 A1 | 9/2002 | Leveque et al. |
| 2002/0136407 A1 | 9/2002 | Denning et al. |
| 2002/0143794 A1 | 10/2002 | Helt |
| 2002/0165736 A1 | 11/2002 | Tolle et al. |
| 2002/0193905 A1 | 12/2002 | Davison et al. |
| 2002/0194024 A1 | 12/2002 | Kleinschmidt |
| 2002/0194025 A1 | 12/2002 | Notelovitz |
| 2002/0198473 A1 | 12/2002 | Kumar et al. |
| 2003/0021417 A1 | 1/2003 | Vasic et al. |
| 2003/0039362 A1 | 2/2003 | Califano et al. |
| 2003/0041241 A1 | 2/2003 | Saito |
| 2003/0046114 A1 | 3/2003 | Davies et al. |
| 2003/0074564 A1* | 4/2003 | Peterson ............ G06F 19/322 713/182 |
| 2003/0081247 A1 | 5/2003 | Sharma |
| 2003/0097358 A1 | 5/2003 | Mendez |
| 2003/0120652 A1 | 6/2003 | Tifft |
| 2004/0034550 A1 | 2/2004 | Menschik et al. |
| 2004/0088355 A1 | 5/2004 | Hagan et al. |
| 2004/0117215 A1 | 6/2004 | Marchosky |
| 2004/0122726 A1 | 6/2004 | Linde et al. |
| 2004/0122792 A1 | 6/2004 | Salazar |
| 2004/0143594 A1 | 7/2004 | Kalies |
| 2004/0189707 A1 | 9/2004 | Moore et al. |
| 2004/0193905 A1 | 9/2004 | Lirov et al. |
| 2004/0199781 A1 | 10/2004 | Erickson |
| 2004/0215981 A1 | 10/2004 | Ricciardi et al. |
| 2005/0027564 A1 | 2/2005 | Yantis |
| 2005/0065912 A1 | 3/2005 | Cafrelli et al. |
| 2005/0114334 A1 | 5/2005 | Ober et al. |
| 2005/0125317 A1 | 6/2005 | Winkelman, III et al. |
| 2005/0147246 A1 | 7/2005 | Agrawal et al. |
| 2005/0165623 A1 | 7/2005 | Landi et al. |
| 2005/0216313 A1 | 9/2005 | Claud et al. |
| 2005/0234740 A1 | 10/2005 | Krishnan et al. |
| 2005/0234909 A1 | 10/2005 | Bade et al. |
| 2005/0236474 A1 | 10/2005 | Onuma et al. |
| 2005/0256740 A1 | 11/2005 | Kohan et al. |
| 2005/0256741 A1 | 11/2005 | Kohan et al. |
| 2005/0256742 A1 | 11/2005 | Kohan et al. |
| 2005/0268094 A1 | 12/2005 | Kohan et al. |
| 2005/0288964 A1 | 12/2005 | Lutzen et al. |
| 2006/0004656 A1 | 1/2006 | Lee |
| 2006/0004739 A1 | 1/2006 | Anthony et al. |
| 2006/0026156 A1 | 2/2006 | Zuleba |
| 2006/0059368 A1* | 3/2006 | Fayad ............... G06F 21/72 713/189 |
| 2006/0178892 A1 | 8/2006 | Oon |
| 2006/0179073 A1 | 8/2006 | Kimura |
| 2007/0073811 A1 | 3/2007 | Rubin et al. |
| 2007/0282951 A1* | 12/2007 | Selimis ............... H04L 67/06 709/205 |
| 2008/0091474 A1 | 4/2008 | Ober et al. |
| 2008/0137860 A1* | 6/2008 | Silvernail ............. H04W 12/04 380/270 |
| 2008/0147554 A1 | 6/2008 | Stevens et al. |
| 2010/0114607 A1 | 5/2010 | Kress et al. |
| 2010/0217973 A1 | 8/2010 | Kress et al. |

FOREIGN PATENT DOCUMENTS

| | | |
|---|---|---|
| EP | 0884670 B1 | 5/1998 |
| EP | 0869637 A2 | 10/1998 |
| EP | 1026603 A2 | 8/2000 |
| EP | 1253544 A1 | 10/2002 |
| EP | 1321883 A3 | 2/2004 |
| JP | 6083847 A | 3/1994 |
| JP | 9-297795 | 11/1997 |
| JP | 10021302 A | 1/1998 |
| JP | 10254807 | 9/1998 |
| JP | 2000513463 | 10/2000 |
| JP | 2000324094 | 11/2000 |
| JP | 2000514938 | 11/2000 |
| JP | 2002032473 | 1/2002 |
| JP | 2003005645 | 1/2003 |
| JP | 2003173376 | 6/2003 |
| JP | 2007056989 | 3/2007 |
| JP | 2011238064 | 12/2007 |
| JP | 2008147364 | 6/2008 |
| JP | 2010232811 | 10/2010 |
| JP | 2001525614 | 12/2011 |
| JP | 2011250165 | 6/2013 |
| WO | 9105397 | 4/1991 |
| WO | WO-9515628 A1 | 6/1995 |
| WO | 9641288 | 6/1996 |
| WO | WO-9641275 A1 | 12/1996 |
| WO | WO-9642059 A1 | 12/1996 |
| WO | 9735271 | 3/1997 |
| WO | 9802837 | 1/1998 |
| WO | 9838910 | 9/1998 |
| WO | 9937054 | 7/1999 |
| WO | 0045317 | 1/2000 |
| WO | 0118730 A1 | 9/2000 |
| WO | WO-0077642 A1 | 12/2000 |
| WO | WO-0118631 A1 | 3/2001 |
| WO | 0129692 | 4/2001 |
| WO | 0139075 | 5/2001 |
| WO | 0141353 | 6/2001 |
| WO | 02063823 | 8/2002 |
| WO | 2004059555 | 7/2004 |
| WO | 2007145010 | 9/2011 |

OTHER PUBLICATIONS

National Institute of Standards and Technology (NIST), "Secure Hash Standard" Federal Information Processing Standards Publication 180-2 (+ Change Notice to include SHA-224), Aug. 1, 2002; pp. i-iv and 1-79.

(56) References Cited

OTHER PUBLICATIONS

U.S. Patent and Trademark Office, Office Action for U.S. Appl. No. 09/665,752, May 5, 2004, 5 pgs.
U.S. Patent and Trademark Office, Office Action for U.S. Appl. No. 09/665,752, Mar. 4, 2005, 6 pgs.
U.S. Patent and Trademark Officer, Office Action for U.S. Appl. No. 09/665,752, Dec. 16, 2005, 4 pgs.
U.S. Patent and Trademark Office, Office Action for U.S. Appl. No. 09/665,752, Mar. 16, 2007, 7 pgs.
U.S. Patent and Trademark Office, Office Action for U.S. Appl. No. 09/665,752, Jan. 25, 2008, 7 pgs.
U.S. Patent and Trademark Office, Office Action for U.S. Appl. No. 09/665,752, Dec. 8, 2008, 8 pgs.
J.D. Halamka, P. Szolovits, D. Rind, and C. Safran, A WWW Implementation of National Recommendationsa for Protecting Electronic Health Information, Journal of the American Medical Informatics Association, vol. 4, No. 6, Nov./Dec. 1997, pp. 458-464.
R. Anderson, The DeCODE Proposal for an Icelandic Health Database, Oct. 20, 1998, pp. 1-12, www.decode.is.
H. Bouzelat, C. Quantin and L. Dusserre, Extraction and Ananymity Protocol of Medical File, Proceedings of the American Medical Informatics Association Annual Fall Symposium, 1996, pp. 323-327, AMIA, Inc.
K.R. Iversen and T.O. Grotan, Socio-technical aspects of the use of health related personal information for management and research, International journal of Bio-Medical Computing, vol. 43, 1996, pp. 83-91, Elsevier Science Ireland Ltd.
A. Ohrn and L. Ohno-Machado, Using Boolean reasoning to ananymize databases, Artificial Intelligence in Medicine, vol. 15, 1999, pp. 235-254, Elsevier Science B.V.
K. Kahl, G. Dickson, J. Kebisek and M. Powell, Bar code tracking system enhances record- and film-handling productivity, Top Health Rec Manage, vol. 12, No. 3, Mar. 1992, 1 pg., St. Joseph's Hospital, Milwaukee, WI, PubMed—indexed for Medline.
E.T. Carroll, S. Wright, C. Zakoworotny, Securely Implementing Remote Access within Health Information Management, Journal of AHIMA, vol. 69, No. 3, Mar. 1998, pp. 46-49, copied from the National Library of Medicine.
Unique Health Identifier for Individuals, U.S. Department of Health and Human Services, A White Paper, pp. 1-32, http://epic.org/privacy/medical/hhs-id-798.html.
English Translation of Japanese Office Action for co-pending application, Reference No. B025547, Mailing No. 571403, Mailing Date: Aug. 10, 2010, Patent Application No. 2001-525614.
S. Chaudhuri, et al: An overview of Data Warehousing and OLAP Technology, Sigmod Record, Sigmod, New York, NY, US, vol. 26, No. 1, Mar. 199, (Mar. 1997), pp. 65-74, XP002193792, ISSN: 0163-5808.
V.M. Brannigan and B. R. Beier, Patient privacy in the era of medical computer networks: a new paradigm for a new technology, Proceedings of the Eighth World Congress on Medical Informatics, vol. 8, No. 8, Jul. 23, 1995, Jul. 27, 1995, pp. 640-643, XP009040274, Vancouver, British Columbia, Canada, ISSN: 1569-6332.
C. Quantin, et al. How to ensure data security of an epidemiological follow up: quality assessment of an anonymous record linkage procedure, International Journal of Medical Informatics, Elsevier Scientific Publishers, Shannon, IR, vol. 49, No. 1, Mar. 1998, pp. 117-122, XP004149470, ISSN: 1386-5056.
R. J. Anderson, A security policy model for clinical information systems, Security and Privacy, 1996, Proceedings, 1996 IEEE Symposium on Oakland, CA, USA May 6-8, 1996 (May 6, 1996), pp. 30-43, XP010164923, ISBN: 0-8186-7417-2.
Supplementary European Search Report of EP 00 96 5216.
International Search Report of PCT/US00/25818.
Secure Hash Standard, National Institute of Standards and Technology, Aug. 1, 2002, pp. i-iv and 1-79, Federal Information Processing Standards Publication 180-2 (+Change Notice to include SHA-224).
HMS PxDx, Health Market Science, A Health Market Science Targeting Solution, 2 pgs., www.healthmarketscience.com.
Why Clearinghouses Transmit Electronic Claims to Insurance Carriers, and Why the Service They Provide is Essential to Medical Practices, Electronic Claim Clearinghouses, MPM Soft, Practice Billing Software, pp. 1-7, www.mpmsoft.com/EDI/clearinghouse.htm, printed Jan. 5, 2009.
Vector One: Prescriber Extract (VOPEX), 2 pgs., Verispan, www.ehealthlist.com.
Physicians Who Perform Medical Procedures, From Direct Medical Data, 1 pg., www.DMDdata.com.
Physicians Treating Patients by Diagnostic Treatement Code ICD9, From Direct Medical Data, 1 pg., www.DMDdata.com.
VOPEX, Vector One: Prescriber Extract, SDI, 1 pg., SDI Healthcare Profiling Solutions Group, www.ehealth.com.
Max G. Arellano, MA, and Gerald I. Weber, PhD, "Issues in Identification and Linkage of Patient Records Across an Integrated Delivery System," Journal of Healthcare Information Management, vol. 12, No. 3, Fall 1998.
Claycamp et al., Simulation Techniques in the Analysis of Marketing Strategy, Applications of the Sciences in Marketing Management (NO DATE).
Hauser et al., Application, Predictive Test, and Strategy Implications for a Dynamic Model of Consumer Response. Marketing Science, vol. 1, No. 2, 1982.
IBM DB2 Universal Database, SQL Ref vol. 1 v 8.2 , 2004—833 pages.
Oracle7 Release 7.3.4 Documentation Library (converted from htm files), 1997 (NO NAME)—2000 PAGES.
Oracle7 Server Concepts Release 7.3, Feb. 1996—516 PAGES.
Tanenbaum A., "Computer Networks 3rd Edition", Prentice-Hall Inc., 1996—BOOK.
Ullman, Pfleeger, Principles of Database Systems, 2d Ed. pp. 216-219; Security in Computing, pp. 327-334, 364-365 (NO DATE)—WON'T UPLOAD.
European Search Report dated Oct. 30, 2015 for corresponding European Patent Application No. 15155354.2, 7 pages.
"Person Identification Service (PIDS) (a.k.a. Patient Identification Service)", OMG CORBAmed DTF, Feb. 12, 1998 (NO NAME).
U.S. Appl. No. 11/122,581, filed Jan. 21, 2010 Amendment and Request for Continued Examination (RCE).
U.S. Appl. No. 11/122,581, filed Dec. 31, 2008 Non-Final Office Action.
U.S. Appl. No. 11/122,581, filed May 29, 2009 Response to Non-Final Office Action.
U.S. Appl. No. 11/122,581, filed Sep. 2, 2009 Final Office Action.
U.S. Appl. No. 11/122,589, filed Feb. 14, 2011 Amendment and Request for Continued Examination (RCE).
U.S. Appl. No. 11/122,589, filed Aug. 13, 2010 Non-Final Office Action.
A. Ohrm and L. Ohno-Machado, Using Boolean reasoning to anonymize databases, Artificial intelligence in Medicine, vol. 15, 1999, DD. 235-254, Elsevier Science B.V.
Allen, Computers & Security, Trusted Oracle—Multilevel Secure Data Management for Military Computing. vol. 70, Issue 3, pp. 271-275, May 1991.
Amendment and Response and Request for Continued Examination (RCE) filed Dec. 10, 2009 for U.S. Appl. No. 11/122,589.
Amendment and Response filed Apr. 6, 2009 for U.S. Appl. No. 11/122,589.
Amendment and Response filed May 27, 2010 for U.S. Appl. No. 11/122,589.
Amendment and Response filed Oct. 23, 2009 for U.S. Appl. No. 11/122,565.
Amstutz, Management, Computers, and Market Simulation, Applications of Management Sciences In Marketing, 1970.
*Armstrong, Brief* vs. *comprehensive descriptions in measuring intentions to purchase*. Journal of Marketing Research, vol. 8, Issue 1, Feb. 1, 1971.
Atkins et al., Pharmaceutical Marketing and Media. Automation in Pharmaceutical Marketing, 1968.
Balog, Sprinter Mod III: A Model for the Analysis of New Frequently Purchased Consumer Products. Operations Research, vol. 18, No. 5, Jul. 1966.

(56) References Cited

OTHER PUBLICATIONS

Berger, Andreas, "Privacy Protection for Public Directory Services", Computer Networks and ISDN Systems 30, 1998.
Bertino and Foscoli, "Index Organizations for Object-Oriented Database Systems", IEEE Transactions on Knowledge and Data Engineering, vol. 7, No. 2, Apr. 1995.
Blattberg et al., Tracker: An Early Test Market Forecasting and Diagnostic Model for New Product Planning. Journal of Marketing Research, vol. 15, Issue 2, May 1978.
Bobrowski, Mastering Oracle7 & Client-Server Computing, 1994.
Borking, John, et al., Privacy-Enhancing Technologies: the Path to Anonymity, vol. II. Registratiekamer, Netherlands, Aug. 1995.
Brandt et al., Anonymous and Verifiable Registration in Databases, May 1988.
Brice et al., Choice-Adapted Preference Modelling. 2000 Sawtooth Software Conference Proceedings, 2000.
Chung, Yun-Chung, et al., Intrinsic Image Extraction from a Single Image. Journal of Information Science and Engineering 25, 1939-1953 (2009).
Claycamp et al., Prediction of New Product Performance: An Analytical Approach, VI Journal of Marketing Research 414-20, 1969.
Communication Pursuant to Article 94(3) EPC dated Oct. 23, 2013 from corresponding European Patent Application No. 05 776 883.0, 6 pages.
Crosse, Marcia, et al., Medical Records Privacy, Access Needed for Health Research, but Oversight of Privacy Protections is Limited. U.S. General Accounting Office, Report to Congressional Requesters, GAO/HEHS-99-55, Feb. 24, 1999.
Dalenius, Tore, and Steven Reiss, Data Swapping—a Technique for Disclosure Control (NO DATE).
Dalrymple et al., Record Linkage in a Regional Mental Health Planning Study: Accuracy of Unique Identifiers, Reliability of Sociodemographics, and Estimating Identification Error. Journal of Mental Health Administration Thousand Oaks, vol. 21, Issue 2, 1994.
Denning, Cryptography and Data Security, 1982.
Denning, Field Encryption and Authentication (NO DATE).
Djordjevic (Oracle Identity and Security Management (NO DATE).
Dussere L., Quantin Co. & Bouzelat H., A One Way Public Key Cryptosystem for the Linkage of Nominal Files in Epidemiological Studies, Proceedings of the Eighth World Congress on Med. Informatics, 1995, pp. 644-647.
European Search Report dated Jul. 10, 2012 from EP Application No. 05 752 085.0, 6 pages.
Evans, Josie and Thomas MacDonald, Record-Linkage for Pharmacovigilance in Scotland. Journal of Clinical Pharmacology 47, 1999.
Fair, M.E., Record Linkage in the National Dose Registry of Canada. European Journal of Cancer, vol. 33, Suppl. 3, 1997.
Final Rejection mailed Jun. 10, 2009 for U.S. Appl. No. 11/122,589.
Final Rejection mailed Nov. 12, 2009 for U.S. Appl. No. 11/122,565.
Gabrieli, Guide for Unique Healthcare Identifier Model. Journal of Clinical Computing, vol. 21, No. 5, 1993.
Gertz, ECS 289F Database Systems, Security in Commercial Database Systems Chap. 3, Lecture, 1998.
Hamburg et al., Computer Model for New Product Demand, Harvard Business Review 107-115, 1967.
Hamilton, Deborah, "Identification and Evaluation of the Security Requirements in Medican Application", IEEE Symposium on Computer-Based Medican Systems.
Harvard Business School Case Study Johnson Wax: Enhance (A), revised Aug. 2, 1999.
Hauser et al., A Normative Methodology for Modeling Consumer Response to Innovation. Operations Research, vol. 25, No. 4, Jul. 1977.
Hauser et al., Application of the "Defender" Consumer Model. Marketing Science, vol. 3, No. 4, 1984.
Hauser et al., Consumer Oriented Transportation Service Planning: Consumer Analysis and Strategies. Applications of Management Science, vol. 1, 1981.
Hauser et al., Dynamic Analysis of Consumer Response to Marketing Strategies. Management Science, vol. 28, No. 5, May 1982.
Herting, Robert and Barnes, Mike, Large Scale Database Scrubbing Using Object Oriented Software Components. Journal of the American Medical Informatics Association, 1998.
Hoffman, The Formulary Model for Flexible Privacy and Access Controls, 1971.
Holman et al., "Population-Based Linkage of Health Records in Western Australia: Development of a Health Services Research Linked Database", Australian and New Zealand Journal of Public Health, vol. 23, No. 5, Oct. 1999.
International Search Report for PCT/US02/06268 dated Feb. 26, 2003.
International Search Report mailed Feb. 6, 2007 in International Application No. PCT/US05/16094, 2 pages.
Jaro, Matthew, Probabilistic Linkage of Large Public Health Data Files. Statistics in Medicine, vol. 14, 1995.
Jawade et al., Securing Anonymous and Confidential Database through Privacy Preserving Updates. International Journal of Applied Information Systems, 2013.
Joshi et al., ScalParC: A New Scalable and Efficient Parallel Classification Algorithm for Mining Large Datasets, Univ. of Minn. Supercomputing Inst. (UMSI 98/14), pp. 1-20, Feb. 1998.
Keller et al., An Algorithm for Matching Anonymous Hospital Discharge Records Used in Occupational Disease Surveillance: Anonymous Record Matching Algorithm. American Journal of Industrial Medicine 20, 1991.
Kerkri, Elmostafa, et al., Application of the Medical Data Warehousing Architecture Epidware to Epidemiological Follow-Up: Data Extraction and Transformation. Medical Informatics Europe (1999).
Kohane, Isaac, et al., Health Information Identification and De-Identification Toolkit. Journal of the American Medical Informatics Association, 1998.
Kontzalis, Identification of key attributes, gap analysis and simulation techniques in forecasting market potential of ethical pharmaceutical products, International Journal of Forecasting 8 243-249, 1992.
Kotler, Computer Simulation in the Analysis of New-Product Decisions (NO DATE).
Kotz, David, Technological Implications for Privacy, Jan. 3, 1999.
Lawrenson et al., Clinical Information for Research; the Use of the General Practice Databases. Journal of Public Health Medicine, vol. 21, No. 3, (1999).
Lennon, Functional Magic—Tips and Tricks with Oracle 7 Stored Procedures, 1996.
Levi, Albert, Design and Performance Evaluation of the Nested Certification Scheme and Its Application in Public Key Infrastructures. Ph.D. Dissertation, 1999.
Lilien et al., Bayesian Estimation and Control of Detailing Effort in a Repeat Purchase Diffusion Environment. Management Science, vol. 27, No. 5, May 1981.
Lilien et al., Marketing Decision Making, A model-Building Approach, 1983.
Lilien et al., Marketing Engineering—Computer Assisted Marketing Analysis and Planning, 1998.
Lilien et al., Marketing Models, 1992.
Lowrance, William, "Privacy and Health Research" (1998).
Mahajan et al., Innovation Diffusion and New Product Growth Models in Marketing. Journal of Marketing, vol. 43, No. 4, 1979.
McDonald, Clement et al., The Regenstrief Medical Record System: A Quarter Century Experience. International Journal of Medical Informatics 54, 1999.
Meax, Eleanor, Encrypting Personal Identifiers. Health Services Research 29:2, Jun. 1994.
Medical Radar International, Mar. 29, 1997.
Medical Radar, Guide to Success, Mar. 2, 1999.
Merkle, R. et al. "On the Security of Multiple Encryption" Communications of the ACM, vol. 24 No. 7, Jul. 1981, pp. 465-467.
Montgomery et al., Management Science in Marketing, 1969.
Muse et al., Evaluating the Quality of Anonymous Record Linkage Using Deterministic Procedures with the New York State AIDS Registry and a Hospital Discharge File. Statistics in Medicine, vol. 14, 1995.

(56) References Cited

OTHER PUBLICATIONS

Nisbett et al., Telling More than We Can Know: Verbal Reports on Mental Processes. Psychological Review, vol. 84, No. 3, May 1977.
Non-Final Rejection mailed Apr. 23, 2009 for U.S. Appl. No. 11/122,565.
Non-Final Rejection mailed Apr. 27, 2009 for U.S. Appl. No. 11/122,564.
Non-Final Rejection mailed Feb. 9, 2010 for U.S. Appl. No. 11/122,589.
Non-Final Rejection mailed Oct. 27, 2008 for U.S. Appl. No. 11/122,589.
Notice of Appeal filed May 12, 2010 for U.S. Appl. No. 11/122,565.
Office Action dated Feb. 5, 2015 from Australian Patent Application No. 2011250762, 4 pages.
Office Action dated Jul. 28, 2014 from Canadian Patent Application No. 2564313, 5 pages.
Office Action dated Sep. 23, 2014 from Australian Patent Application No. 2011250762, 3 pages.
Office Action dated Sep. 24, 2014 from Australian Patent Application No. 2011250762, 3 pages.
Office Action in Australian Application No. 2011247850, mailed Sep. 4, 2014, 4 pages.
Office Action in Canadian Application No. 2564317, mailed Aug. 20, 2013, 3 pages.
Office Action in Canadian Application No. 2564317, mailed Jul. 28, 2014, 3 pages.
Ohrn, Aleksander and Lucila Ohno-Machado, Using Boolean Reasoning to Anonymize Databases. Artificial Intelligence in Medicine 15, 1999.
Patent Examination Report No. 1 dated Aug. 23, 2013 from corresponding Australian Patent Application No. 2011250762, 3 pages.
Perry et al., Understanding Oracle Chapters 1,11,14, 1989.
Pfleeger, Security in Computing (NO DATE).
Pommerening et al., Pseudonyms for Cancer Registries, Methods of Information In Medicine 112-121, 1996.
Privacy Data: the Data Encryption Standard Provides Valuable Protection. U.S. General Accounting Office, Program Evaluation and Methodology Division, Transfer Paper 8, Mar. 1987.
Proceedings of the 1993 Public Health Conference on Records and Statistics, Jul. 19, 1993.
Quantin et al., A Computerized Record Hash Coding and Linkage Procedure to Warrant Epidemiological Follow-Up Data Security. Medical Informatics Europe, 1997.
Quantin et al., Automatic Record Hash Coding and Linkage for Epidemiological Follow-up Data Confidentiality, 37 Methods of Information in Medicine 271-277, 1998.
Quantin, C., et al., Irreversible Encryption Method by Generation of Polynomials. Medical Informatics, vol. 21, No. 2, 1996.
Rao et al., Forecasting with a Repeat Purchase Diffusion Model, Management Science vol. 34, No. 6, 1988.
Samarati, Pierangela and Latanya, Sweeney, Generalizing Data to Provide Anonymity when Disclosing Information (1998).
Samarati, Pierangela and Latanya, Sweeney, Protecting Privacy when Disclosing Information: k-Anonymity and Its Enforcement through Generalization and Suppression (1998).
Segev et al., A Framework for Join Pattern Indexing in Intelligent Database Systems, IEEE Trans. on Knowledge and Data Eng'g, vol. 7, No. 6 at pp. 941-947, Dec. 1995.
Silk et al., Pre-Test-Market Evaluation of New Packaged Goods: A Model and Measurement Methodology. Journal of Marketing Research, vol. 15, Issue 2, May 1978.
Smith and Eloff, Security in Health-Care Information Systems—Current Trends. International Journal of Medical Informatics 54, 1999.
Smith, An Inquiry into the Nature and Causes of the Wealth of Nations (HeinOnline 9th ed. 1799).
Spafford, Observing Reusable Password Choices, Jul. 31, 1992.
Spenser, W., The Health Information System (HIS). Computer Programs in Biomedicine 5, 1976.
Stanberry, Ben, The Legal and Ethical Aspects of Telemedicine 2: Data Protection, Security and European Law. Journal of Telemedicine and Telecare 1998, Nov. 23, 1997.
Subramanian, Ashok, et al., Use of the World Wide Web for Multisite Data Collection. Academic Emergency Medicine, vol. 4, No. 8, Aug. 1997.
Sweeney, Latanya, "Datafly: A System for Providing Anonymity in Medical Data" (1997).
Sweeney, Latanya, Guaranteeing Anonymity when Sharing Medical Data, the Datafly System (1997).
Sweeney, Latanya, Maintaining Patient Confidentiality when Sharing Medical Data Requires a Symbiotic Relationship between Technology and Policy. Massachusetts Institute of Technology Artificial Intelligence Laboratory, Working Paper No. AIWP-WP344b, May 1997.
Sweeney, Latanya, Replacing Personally-Identifying Information in Medical Records, the Scrub System. Journal of the American Medical Informatics Association, 1996.
Technology and Informatics 68, Medical Informatics Europe '99 (NO NAME).
Thelot, A general solution to the linkage of anonymous data. C.R. Acad. Sci. Paris, t. 310, Serie III, 1990.
Trusted Oracle7 Release 7.1, Discussion Forum Thread, Jan 16, 2007.
Tsukagoshi, Noboru, "Ubiquitous computing and distribution system", Magazine of "Logistic System", Japan Logistics System Institute, Jan. 30, 2004, 13(2): 32-38.
U.S. Patent and Trademark Office, Notice of Allowance for U.S. Appl. No. 09/665,752, Feb. 27, 2013, 13 pgs.
Ullman, Principles of Database Systems, 2d Ed. pp. 216-219, 1982.
Urban et al., Design and Marketing of New Products, 1993.
Urban et al., Prelaunch Forecasting of New Automobiles. Management Science, vol. 36, No. 4, Apr. 1990.
Urban et al., Premarket Forecasting of Really-New Products, 60 Journal of Marketing 47-60, 1996.
Urban, Sprinter Mod III: A Model for the Analysis of New Frequently Purchased Consumer Products. Operations Research, vol. 18, No. 5, Sep. 1970.
Valduriez, Join Indices, ACM Trans. On Database Sys., vol. 2, No. 2 at pp. 218, 246 (1987).
Vinod, ATMSIM: A Simulator for ATM Networks. Master's Thesis (Apr. 1995).
Wind et al., Courtyard by Marriott: Designing a Hotel Facility with Consumer-Based Marketing Models. Interfaces 19, Jan. 1989.
Wohlmacher and Pharow, Applications in Health Care Using Public-Key Certificates and Attribute Certificates.
X. Thirion, R. Sambuc & J.L. San Marco, Epidemiology and anonymity: a new method, Rev. Epidem. Et. Sante Publ., 1988, pp. 36-42.
Apr. 16, 2015 Patent Examination Report No. 5 from corresponding Australian Patent Application No. 2011250761, 3 pages.
Office Action dated May 11, 2015 from corresponding European Patent Application No. 05754019.7, 4 pages.
Newswire, "CUNO Posts Record Results" New York, Dec. 11, 1997, p. 1 (seven pages total).
Business World, "Fighting to stay on top," Manila, Dec. 11, 1996, p. 25 (four pages total).
Record Linkage Techniques—1997, Proceedings of an International Workshop and Exposition, Federal Committee on Statistical Methodology, Office of Management and Budget, Washington, DC (1997).

\* cited by examiner

FIG. 4

SYSTEM AND METHOD FOR THE PROTECTION AND DE-IDENTIFICATION OF HEALTH CARE DATA

CROSS-REFERENCE TO RELATED APPLICATION

This application claims priority under 35 U.S.C. §119(e) to U.S. Provisional Patent Application No. 60/875,392, entitled "System and Method for the Protection and De-Identification of Health Care Data" by Andrew E. Kress et al., filed on Dec. 18, 2006, the entire disclosure of which is incorporated herein by reference.

FIELD OF THE INVENTION

The present invention relates to a system and a method for protecting data. In particular, the present invention relates to a system and a method for protecting healthcare data, purging the data of patient identifiable information, and associating the healthcare data of the same person.

BACKGROUND OF THE INVENTION

An increasing amount of patient healthcare data regarding disease and treatment is being electronically entered and recorded. For example, a healthcare provider may electronically submit healthcare data for the purpose of receiving payment for services rendered. The data generally flows from the healthcare provider to a clearinghouse or a provider of electronic data interchange and related services. Healthcare data submitted can include standardized codes to describe the diagnosis made, services performed, or products used.

As patient data regarding disease and treatment becomes more widely recorded and available, linking data for individual patients from different data sources created at different times would be advantageous, for example, when a researcher wants to study certain variables, such as patients' diagnoses, procedures performed, or drugs prescribed.

However, the Health Insurance Portability and Accountability Act of 1996 (HIPAA) restricts entities covered under HIPAA from disclosing protected health information ("PHI"). The disclosure of PHI is regulated because it is healthcare data with personally identifiable information ("PII"). Many data sources would be considered covered entities because the data sources produce information which may contain PHI, and PHI through its associated PII can be used to positively identify a person. Such information containing PII and concerning individual privacy are strictly protected by HIPAA. Under HIPAA, covered entities cannot disclose PII to third parties, except in limited circumstances, such as to other authorized entities for billing purposes. Thus, healthcare data used by non-covered entities for research, analysis, and/or reporting needs to be de-identified so that the data is no longer considered PII. Consequently, direct identifiers, such as names, elements of addresses (except zip codes if they cover a sufficiently large population), birth dates, social security numbers, insurance policy numbers, license numbers, or any other unique identifier that may allow patient identification, must be removed. Thus, researchers are limited to data which may not include a particular desired variable, such as the prevalence of a particular disease in a particular area because any demographic data, even indirect identifiers, appended to de-identified patient data increases the risk of identifying an individual. As a result, researchers are limited to data without relevant demographic variables that they may wish to study.

Thus under HIPAA, the healthcare data transmitted by covered entities must be de-identified so that it no longer contains PII. HIPAA stipulates two methods for de-identifying data. The first method is based on the safe harbor provision, which directs the removal of 18 enumerated identifiers, such as, name, geographic subdivision smaller than a state, dates directly related to an individual phone numbers, fax numbers, email addresses, social security numbers, medical record numbers, health plan beneficiary numbers, account numbers, certificate/license numbers, vehicle identifiers and serial numbers, device identifiers and serial numbers, web universal resource locators, Internet protocol address numbers, biometric identifiers, full face photographic and comparable images, and other unique identifiers. The second method is based on statistical de-identification. An entity covered under HIPAA may determine that the health information is not individually identifiable health information only if a person with appropriate knowledge of and experience with generally accepted statistical and scientific principles and methods for rendering information individually unidentifiable, applying such principles and methods, (1) determines that the risk is very small that the information could be used, alone or in combination with other reasonably available information, by an anticipated recipient to identify an individual who is the subject of the information, and (2) documents the methods and results of the analysis that justify such a determination, as described in "HIPAA Certification for SDI's De-Identification Technology" by Fritz Scheuren, Ph.D. and Patrick Baier, D. Phil, dated Jun. 4, 2007.

As described by Scheuren and Baier, known methods append additional information to the de-identified patient data. One method appends additional information in a non-specific way such as with the zip code or other grouping information, as discussed in the "Description of the Related Art" in U.S. Patent Application Pub. No. 2004/0199781, entitled "Data Source Privacy Screening Systems and Methods," by Erickson et al. Another method appends only limited variables in order to minimize the risk of identification, as discussed in U.S. Patent Application Pub. No. 2004/0199781. The disadvantages of these approaches are that (1) they assume that all individuals in a particular group share the same appended characteristic data, (2) they limit the number of discrete variables that can be included in any analysis, (3) they require a very high degree of oversight and review by an approved statistician, and/or (4) they carry a risk of re-identification, as the party who holds the merged data may have enough data available to possibly re-identify an individual in violation of HIPAA through combining the data with demographic or other available variables.

Thus, there continues to be a need for a system and a method that allows associating of patient healthcare data from different data sources at different times but avoids using PII that can be used to identify the patient.

SUMMARY OF THE INVENTION

Accordingly, an aspect of the present invention is to provide a system and a method for protecting and de-identifying healthcare data. Another object of the present invention is to correlate de-identified healthcare data for a particular patient from several data sources without using PII that can be used to identify the patient.

One embodiment of the present invention provides a system for protecting and de-identifying healthcare data. The system includes a storage device for storing the healthcare data and personally identifiable information for a person; and a processor in communication with the database, the processor generates an anonymous linking code using a keyed hash function and a second hash function, the anonymous linking code based at least in part on a portion of the personally identifiable information, said processor further appending the anonymous linking code to the healthcare data for the person.

Another embodiment of the present invention provides a system for protecting and de-identifying healthcare data. The system includes at least one data source capable of generating an anonymous linking code using a keyed has function and a second hash function, the anonymous linking code based at least in part on a portion of personally identifiable information, the at least one data source capable of transmitting healthcare data with the anonymous linking code appended to the healthcare data; and a data warehouse capable of receiving the healthcare data with the appended anonymous linking code and storing the healthcare data with the appended anonymous linking code, the data warehouse associating the received healthcare data with stored healthcare data by matching appended anonymous linking codes.

Yet another embodiment of the present invention provides a method for protecting and de-identifying healthcare data. The method includes the steps of: using a keyed hash function to convert a portion of personally identifiable information into a first output; using a second hash function to convert the first output into an anonymous linking code; appending the anonymous linking code to the healthcare data; and removing personally identifiable information from the healthcare data.

Yet another embodiment of the present invention provides a system for protecting and de-identifying healthcare data. The system includes a data retrieval module receiving healthcare data and its associated personally identifiable information; an extraction and encryption module in communication with the data retrieval module, the extraction and encryption module extracting portions of personally identifiable information for forming an anonymous linking code and encrypting the portions of the personally identifiable information; a concatenation module in communication with the extraction and encryption module, the concatenation module linking together in a predetermined sequence the portions of the personally identifiable information; a first hash function module in communication with the concatenation module, the first hash function module inputting the portions of the personally identifiable information into a first hash function that converts the portions of the personally identifiable information into a first output; a second hash function module in communication with the first hash function module, the second hash function module inputting the first output into a second hash function that converts the first output into an anonymous linking code; a de-identification module in communication with the second hash function module, the de-identification module appending the anonymous linking code to the healthcare data and substantially removing the personally identifiable information from the healthcare data; an encryption for transmission module in communication with the de-identification module, the encryption for transmission module encrypting for transmission the healthcare data and the appended anonymous linking code; a data transmission module in communication with the encryption for transmission module, the data transmission module transmitting the encrypted healthcare data and appended anonymous linking code on a data pathway; the data pathway in communication with the data transmission module; a data reception module in communication with the data pathway, the data reception module receiving the encrypted healthcare data and appended anonymous linking code from the data pathway; a decryption module in communication with the data reception module, the decryption module decrypting the encrypted healthcare data and appended anonymous linking code; a patient linkage module in communication with the decryption module, the patient linkage module linking healthcare data related to the same person; and a report creation module in communication with the decryption module, the report creation module outputting a report based on the healthcare data.

Other objects, advantages and salient features of the invention will become apparent from the following detailed description, which, taken in conjunction with the annexed drawings, discloses a preferred embodiment of the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is an example report outputted by the system illustrated in FIG. 1; and

DETAILED DESCRIPTION OF THE INVENTION

Referring to FIGS. 1-5, the present invention provides a system and a method for protecting and de-identifying healthcare data subject to HIPAA by converting elements of PII into an anonymous linking code that protects the anonymity of the individual associated with the healthcare data. The anonymous linking code is HIPAA-compliant and allows for identification of a unique individual while preserving the anonymity of that individual by forming the anonymous linking code from predetermined portions of PII and replacing PII with the anonymous linking code. The healthcare data is "de-identified" by removing all information considered to be PII. The anonymous linking code is then appended to the healthcare data.

The anonymous linking code allows for linking or associating of healthcare data for a particular person even though the healthcare data has no direct identifiers, comes from different data sources, and was created at different times. The de-identified data with the appended anonymous linking code is sent to a data warehouse that can join several data files at the de-identified patient-specific level. At the data warehouse, the anonymous linking code can be replaced with or augmented by an indexing tag. By replacing the anonymous linking code, which is based on portions of PII, with the indexing tag, the healthcare data is substantially de-identified because it contains no PII, and the anonymous linking code, which is based on portions of PII, is replaced by the indexing tag. Data can then be linked (i.e., associated with other data related to the same person) and clustered without using PII or any data based on PII. The results are then returned to the data source, which can replace the anonymous linking code with PII.

Thus, the present invention prevents an entity having de-identified data that is subject to HIPAA from also having specific data related to an individual. The present invention also prevents a party having data related to an individual from also having HIPAA data at an individual-specific level. By providing data in such a manner, the present invention minimizes the risk of individual re-identification, while allowing the use of highly specific demographic and other information in combination with data subject to HIPAA.

Figure 1:
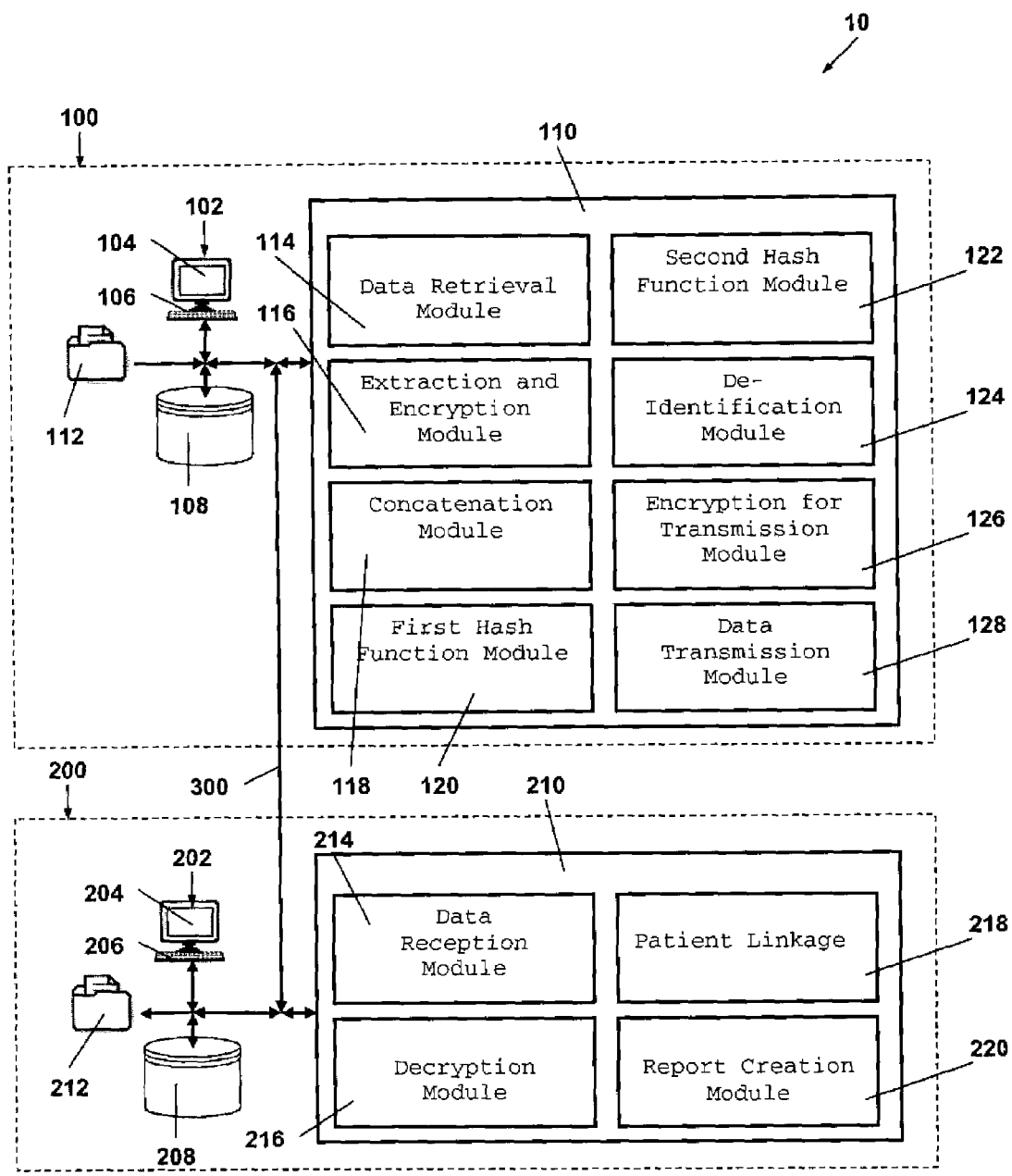
FIG. 1 is a block diagram of a system for protecting and de-identifying healthcare data in accordance with an exemplary embodiment of the invention.

Referring to FIG. 1, a system 10 is provided for protecting and de-identifying healthcare data. The system 10 includes, at least, a data source 100 and a data warehouse 200. The data source 100 includes a user interface 102, a database 108, a processor 110, and healthcare data 112. The data source 100 can be located at a physician's office, a hospital, a pharmacy, a laboratory, a health insurer, a consultancy, or any other similar facility where healthcare data is collected, received, provided, or created. The data source 100 is preferably provided at any facility that is considered to be a covered entity under HIPAA.

HIPAA regulates healthcare data 112 if it contains PHI. The disclosure of PHI is regulated because it contains PII. The healthcare data 112 is data pertaining to the health, condition, disease, treatment, and other similar information of a particular person who is identified by PII. The healthcare data 112 can include, but is not limited to, diagnoses, patient visit information, drug data, procedure data, prescription-specific information, laboratory data, data feeds, test orders, test results, consultant's report, and other similar data related to or associated with the health of the person. The healthcare data 112 can be provided on a standard form, such as CMS-1500/837p, CMS-1450/UB-92/UB-04/837i, NCPDP 5.1, or other similar forms. The healthcare data 112 can also include standardized codes to describe the diagnoses made, services performed, products used, and other relevant information. The healthcare data 112 can be from healthcare insurance claims from pharmacies and physicians. The healthcare data 112 can be from data provided directly by the healthcare provider or from data provided by a central clearinghouse, a payer, a pharmacy benefits manager, or other similar sources of healthcare data 112.

The user interface 102 is in communication with the database 108 and the processor 110. The user interface 102 can be a desktop, handheld, and/or touch screen computing device or any other display and information input device. It has a display 104 and an input device 106. The display 104 can be any device that presents information to the user. The input device 106 can be any device to electronically enter information into the data source 100, such as, but not limited to, a keyboard, touch screen, mouse, scanner, digital camera, or other similar device for transmuting non-electronic information into electronic data.

The database 108 is in communication with the user interface 102 and the processor 110. The database 108 stores information, such as PHI or healthcare data 112 and its associated PII. The database 108 can be separate from the processor 110 or can be stored in memory internal to the processor 110. Though a single database 108 is shown in the embodiment of FIG. 1, more than one database can be provided. If more than one database is provided, each separate database is preferably in communication with each other, the user interface 102, the processor 110, or any combination of these components.

Figure 2:
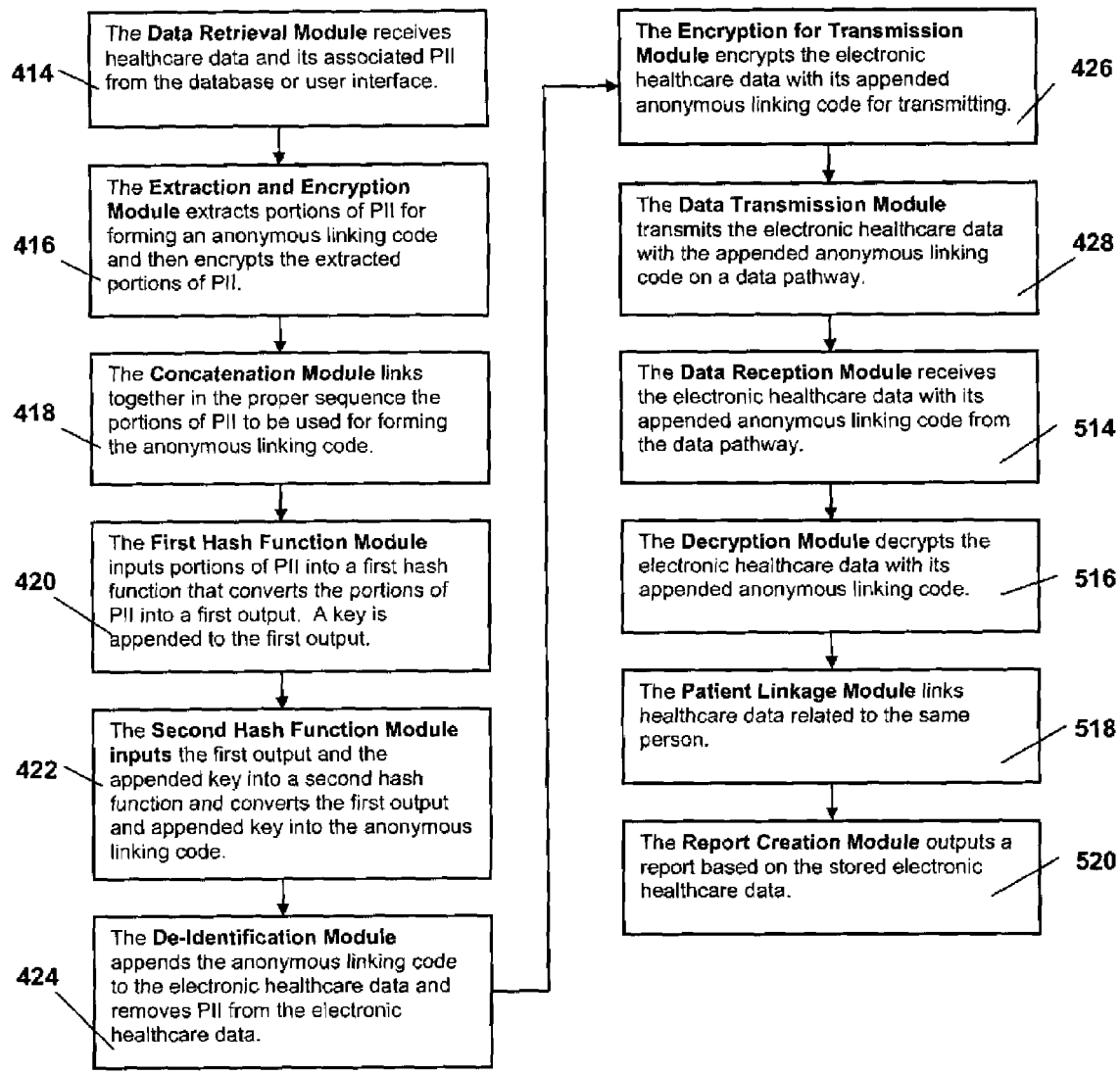
FIG. 2 is a flow diagram showing operations performed by modules of the system illustrated in FIG. 1.

The processor 110 is in communication with the user interface 102 and the database 108. The processor 110 preferably has one or more of the following modules: a data retrieval module 114, an extraction and encryption module 116, a concatenation module 118, a first hash function module 120, a second hash function module 122, a de-identification module 124, an encryption for transmission module 126, and a data transmission module 128. Each of the modules described herein has various sub-routines, procedures, definitional statements, macros, and other similar processes. Software is provided in the processor 110 to implement the system 10 and a method of protecting and de-identifying healthcare data. The software includes programming that embodies the data retrieval module 114, the extraction and encryption module 116, the concatenation module 118, the first hash function module 120, the second hash function module 122, the de-identification module 124, the encryption for transmission module 126, and the data transmission module 128. The description of each of the modules is used for convenience to describe the functionality of the processor 110 and the system 10 overall. Thus, the processes that are performed by each of the modules may be redistributed to one of the other modules, combined together in a single module, or made available in a shareable dynamic link library. FIG. 2 is a flow diagram showing the operations performed by the modules.

The user interface 102, the database 108, and the processor 110 can each be coupled to the Internet or a network such as a local area network (LAN) or wide area network (WAN). The system 10 is not limited to hard-wired connections but can include wireless communication such as radiofrequency (RF), 802.11 (WiFi), Bluetooth or any combination of data communications paths. For example, the data source 100 can be implemented or incorporated as a single device such as a stand-alone personal computer or a PDA or the database 108 can be placed on a remote server coupled to the Internet by hard-wired connections with other components located nearby in wireless communication with the Internet.

The data source 100 replaces PII with a HIPAA-compliant encrypted anonymous linking code that allows for identification of a unique individual while preserving the anonymity of that individual. The anonymous linking code is formed from predetermined portions of PII and appended to the healthcare data 112. Then the healthcare data 112 is de-identified by removing all PII at the data source 100 before the electronic healthcare data is sent to a data warehouse 200.

Figure 3:
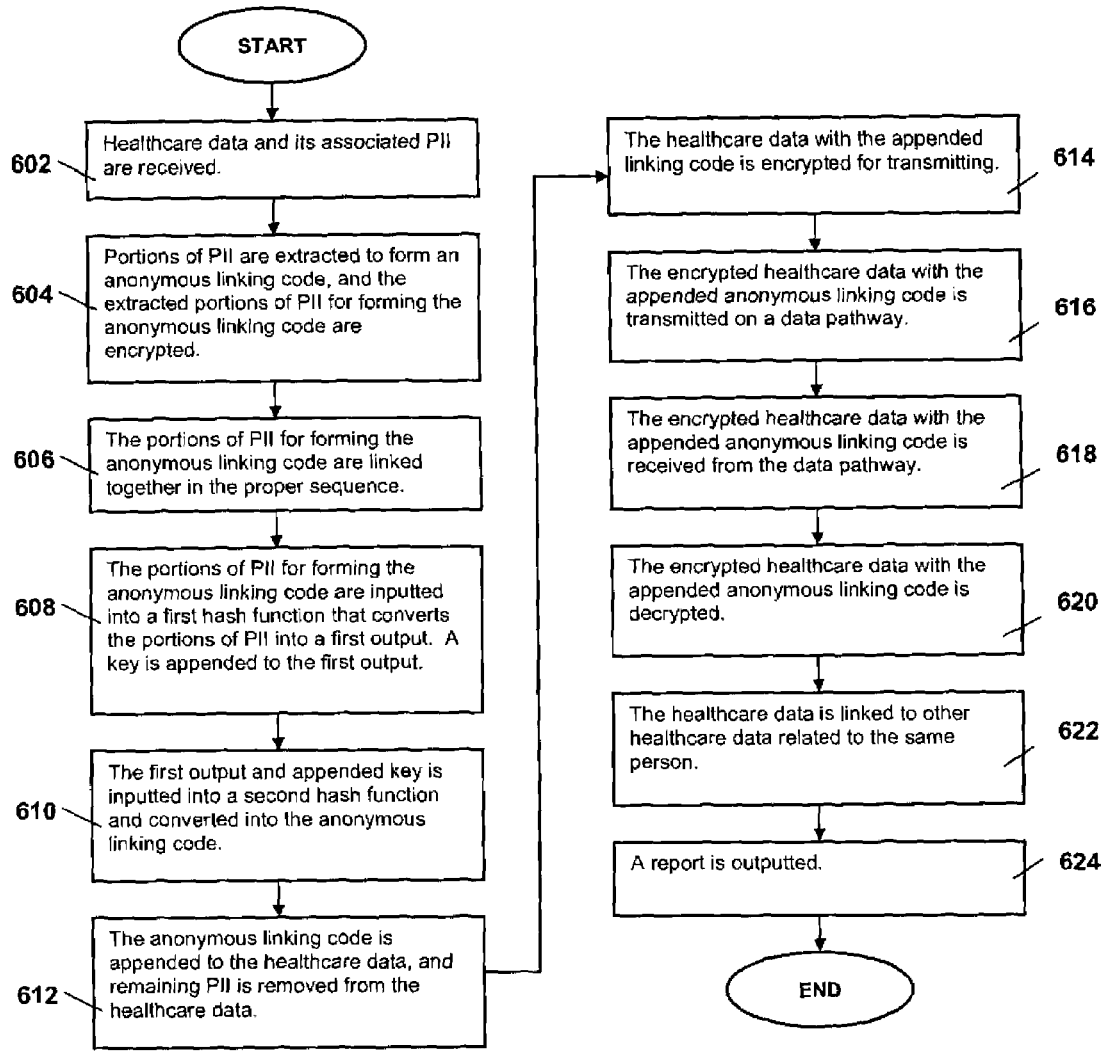
FIG. 3 is a flow diagram of a method for protecting and de-identifying healthcare data in accordance with an exemplary embodiment of the invention.

To describe the system 10 and the method of protecting and de-identifying healthcare data concurrently, reference will be made to FIG. 1 which depicts the system 10, FIG. 2 which shows the operations performed by the system 10, and FIG. 3 which is a flow diagram of the method. In step 602, healthcare data 112 and its associated PII are received. This is performed in the processor 110 by the data retrieval module 114 which retrieves electronic healthcare data, including PHI and its associated PII, from the database 108 or from the user interface 102, step 414. The healthcare data 112 is converted into electronic healthcare data by the input device 106.

Next, in step 604 of the method, portions of PII are extracted to form an anonymous linking code and the extracted portions of PII are encrypted. During extraction, portions of PII required to form the anonymous linking code are identified in the healthcare data 112 and can also be set aside to be converted into the anonymous linking code. In the processor 110, the extraction and encryption module 116 extracts predetermined portions of PII from the electronic healthcare data and encrypts those extracted portions, step 416. The extraction and encryption module 116 copies and stores in the database 108 or in the memory of the processor 110 predetermined portions of PII for converting into the anonymous linking code. In the preferred embodiment, after the predetermined portions of PII required to form the anonymous linking code are stored in the database 108 or in the memory of the processor 110, the electronic healthcare data can be modified so that the predetermined portions of PII are deleted from the electronic healthcare data. For electronic healthcare data made up of bits, the bits representing the predetermined portions of PII are nulled (i.e., the PII is replaced with 0 bits of data).

Predetermined portions of PII are used to create an anonymous linking code (done in step 610) so that there is a functional relationship or dependence between the anonymous linking code and the PII. The functional relationship or dependence allows the same anonymous linking codes to be created by unrelated or separate data sources 100. Thus, each data source 100 will be able to create the same anonymous linking code because each data source 100 creates it from the same predetermined portions of PII. The predetermined portions of PII can be, for instance, the patient's name, birth date, social security number, some other identifying information, or any combination of these. Since in some cases the electronic healthcare data may not include, for example, the birth date or the social security number, the anonymous linking code can be derived from other available portions of PII in the electronic healthcare data. Regardless, the extraction and encryption module 116 extracts predetermined portions of PII from the healthcare data retrieved at step 602 by the data retrieval module 114.

After the predetermined portions of PII are extracted by the extraction and encryption module 116, the extracted predetermined portions of PII are encrypted. The encryption provides further protection of the extracted predetermined portions of PII. Each extracted predetermined portion of PII for forming the anonymous linking code can encrypted individually or collectively. The encryption is preferably done by common techniques, such as character substitution or translation, as described in U.S. Pat. No. 4,979,832 to Ritter, the entirety of which is incorporated herein by reference. The encryption can also be completed by block cipher, hash function, or any other suitable encryption method.

In step 606, the extracted and encrypted portions of PII are assembled together in a predetermined sequence. In the processor 110, the concatenation module 118 concatenates the portions of the PII, step 418. After each portion of PII has undergone encryption in the extraction and encryption module 116, the concatenation module 118 assembles together the encrypted portions of PII. To ensure that each data source 100 creates the same anonymous linking code from the same predetermined portions of PII, the portions of PII must be properly sequenced in the same predetermined sequence prior to inputting into a first hash function in step 608.

In step 608, the extracted, encrypted, and properly sequenced predetermined portions of PII are inputted into the first hash function, step 420. In the processor 110, the first hash function module 120 inputs the extracted and encrypted portions of the PII that have been linked in the proper sequence into the first hash function, and the first hash function converts the extracted, encrypted, and properly sequenced portions of PII into a first output.

The hash function is a cryptographic primitive. Although another cryptographic primitive, such as a block cipher, can be used, the hash function is preferred because it generally has no inverse function that can recover the input from the hash function's output. The hash function maps a bit string of arbitrary length to another bit string of fixed length. Hash functions include Ripe-MD, Whirlpool, Haval, MD4, MD5, and the SHA group of hash functions. Preferably, the first hash function is from the SHA-2 family, in particular, SHA-256 which creates 256 bit hashes. The SHA family of hash functions was designed by the National Institute of Standards and Technology and is a Federal Information Processing Standard, as described by Federal Information Processing Standards Publication 180-2, dated Aug. 1, 2002. Federal Information Processing Standards Publication 180-2 also provides an algorithm and examples for implementing an SHA-256 hash function.

The first output of the first hash function can be, but is not limited to, a character string, a bit string, a base-n number, or any other suitable hash function output. Preferably, the first output is a hexadecimal number. The first hash function is also keyed to prevent deciphering the anonymous linking code back to its constituent predetermined portions of PII. Preferably, a key comprised of a string of random characters is appended to the first output of the first hash function. The key can also be appended to the extracted, encrypted, and properly sequenced portions of the PII before being encrypted by the first hash function. The key is a fixed character string where each character was chosen randomly and independently of other characters in the key. In one exemplary embodiment, the key is a fixed character string of 64 characters where each of the 64 characters is randomly selected from the set of 94 printable, non-blank ASCII characters.

The key must be protected to prevent the anonymous linking code from being decrypted back into the portions of PII used to derive the anonymous linking code. The key can be protected by using an independent third party to choose the key, obfuscating the key in the first hash function module 120, using mathematical algorithms to reconstruct the key when the key is required, or any combination of the above. Alternatively, the key can be transmitted separately before it is used. If the key is transmitted, it can be transmitted via web services, such as SOAP, which is a protocol for exchanging XML-based messages over computer networks, normally using HTTP/HTTPS.

In step 610, after the key is appended to the first output of the first hash function, the first output and the key are inputted into a second hash function. In the processor 110, the second hash function module 122 inputs the first output and the key from the first hash function module 120 into the second hash function that converts the first output and the key into the anonymous linking code, step 422. Inputting the first output and the key into the second hash function provides additional protection by using two hash functions sequentially to convert portions of PII into the anonymous linking code. The second hash function is similar to the first hash function and is implemented substantially in the same way the first hash function is implemented. The output of the second hash function, i.e., the anonymous linking code, can be, but is not limited to, a character string, a bit string, a base-n number, or any other suitable hash function output. Preferably, the anonymous linking code is a bit string. The anonymous linking code can be used in place of PII and appended to healthcare data that is not subject to HIPAA requirements.

Next, in step 612, the anonymous linking code is appended to the healthcare data 112, and any remaining PII is removed from the healthcare data 112. In step 604, described above, only portions of PII required to form the anonymous linking code may have been removed, thus any remaining portions of PII must be removed from the healthcare data 112 so that the data 112 will not be subject to HIPAA. In the processor 110, the de-identification module 124 electronically appends the anonymous linking code to electronic healthcare data and modifies the electronic healthcare data so that any remaining PII is deleted. The processor 110 electronically appends the anonymous linking code to the end of the electronic healthcare data. Thus, for electronic healthcare data represented by bits, the bits representing the anonymous linking code will be at the end of the set of bits representing the electronic healthcare data. In the preferred embodiment, only the portions of PII required to form the anonymous linking code are removed by the extraction and encryption module 116, thus some PII may still need to be removed from the healthcare data. Any remaining direct identifiers are removed from the healthcare data. Direct identifiers include, for example, the name, some parts of the address, the social security number, the insurance policy number, the license number, and other similar identifying information. In embodiments where the electronic healthcare data is represented by bits, the bits representing the remaining PII are nulled. Because the electronic healthcare data is missing data that represented the removed PII, the de-identification module can also shift the remaining data elements to make up for the removed and missing PII data. In the preferred embodiment, the file representing the electronic healthcare data is rewritten into a new file that does not contain any PII.

In step 614, both the healthcare data without PII and its appended anonymous linking code are encrypted for transmission. In the processor 110, the encryption for transmission module 126 encrypts the electronic healthcare data with its appended anonymous linking code for transmitting, step 426. This additional encrypting prior to transmitting further protects the electronic healthcare data and its appended anonymous linking code. The encryption before transmission can be done by using Information Concealment Engine (ICE), Data Encryption Standard (DES), Advanced Encryption Standard (AES), Triple DES, RC5, Blowfish, IDEA, New DES, JAFER, CAST5, FEAL, a block cipher, or any other suitable encryption. Preferably, the encryption before transmission is completed by using ICE, such as Pretty Good Privacy (PGP) encryption.

Then, in step 616, the encrypted healthcare data with its appended anonymous linking code is transmitted on a data pathway 300 to an authorized recipient, in this case the data warehouse 200. In the processor 110, the data transmission module 128 transmits the electronic healthcare data with the appended anonymous linking code on a data pathway 300, step 428. Preferably, the data pathway 300 is secure to prevent interception of protected information. The encrypted electronic healthcare data with its appended anonymous linking code is transmitted through the data pathway 300 to the data warehouse 200 where the electronic healthcare data can be processed into a customizable output in step 624. The data pathway 300 can be, but is not limited to, the Internet or a network such as a local area network (LAN) or wide area network (WAN). The data pathway 300 can include hard-wired connections as well as wireless communication such as radiofrequency (RF), 802.11 (WiFi), Bluetooth or any combination thereof. The data pathway 300 can be any combination of data communications pathways. As described above, the electronic healthcare data with its appended anonymous linking code is preferably transmitted by a secure method, such as File Transfer Protocol (FTP), secure File Service Protocol (FSP), FTPS or FTP/SSL, Gopher, Secure Copy Protocol (SCP), Simple File Transfer Protocol (SFTP), SSH, Trivial File Transfer Protocol (TFTP), and other similar secure data transmission pathways.

The data warehouse 200 processes, stores, and transmits the electronic healthcare data to selected recipients in a customizable output. Processing the electronic healthcare data can include, but is not limited to, cleaning, collecting, classifying, packaging, additional de-identifying, and matching the electronic healthcare data. The data warehouse 200 also distributes the electronic healthcare data to recipients in a requested format. As shown in FIG. 1, the data warehouse 200 includes a user interface 202, a storage device 208, a processor 210, and a report 212. The data warehouse 200 can be located near to or remote from the data source 100. The user interface 202 is similar to the user interface 102 of the data source 100, and thus a detailed description thereof is omitted.

The storage device 208 is in communication with the user interface 202 and the processor 210. The storage device 208 stores healthcare data including electronic healthcare data that was previously received from the data source 100. The stored electronic healthcare data can include the appended anonymous linking codes and/or an indexing tag (described more fully below). Though a single storage device 208 is shown in the embodiment of FIG. 1, more than one storage device can be provided. If more than one storage device is provided, each separate storage device is preferably in communication with each other, the user interface 202, the processor 210, or any combination of these components. Also, in alternate embodiments, the storage device 208 can be the memory associated with the processor 210.

The processor 210 is in communication with the user interface 202 and the storage device 208. The processor 210 preferably has one or more of the following modules: a data reception module 214, a decryption module 216, a patient linkage module 218, and a report creation module 220. Each of the modules described herein has various sub-routines, procedures, definitional statements, macros, and other similar processes. Software is provided in the processor 210 to implement the system 10 and the method. The software includes programming that embodies the data reception module 214, the decryption module 216, the patient linkage module 218, and the report creation module 220. The description of each of the modules is used for convenience to describe the functionality of the processor 210 and the system 10 overall. Thus, the processes that are performed by each of the modules may be redistributed to one of the other modules, combined together in a single module, or made available in a shareable dynamic link library.

The user interface 202, the storage device 208, and the processor 210 can each be coupled to the Internet or a network such as a local area network (LAN) or wide area network (WAN). The system 10 is not limited to hard-wired connections but can include wireless communication such as radiofrequency (RF), 802.11 (WiFi), Bluetooth or any combination of data communications paths. For example, the data warehouse 200 can be implemented or incorporated as a single device such as a stand alone computer or a PDA or the storage device 208 can be placed on a remote server coupled to the Internet by hard-wired connections with other components located nearby in wireless communication with the Internet.

In step 618, the encrypted healthcare data with the appended anonymous linking code is received from the data pathway 300. In the processor 210, the data reception module 214 receives the electronic healthcare data with its appended anonymous linking code from the data pathway 300, step 514.

Next, in step 620, the encrypted healthcare data with its appended anonymous linking code is decrypted. In the processor 210, the decryption module 216 decrypts the electronic healthcare data with its appended anonymous linking code, step 516. The decryption module 216 decrypts the encrypted information which was encrypted by the transmission module 126 in step 614. The anonymous linking code can also be replaced with or augmented by an indexing tag. By replacing the anonymous linking code, which is based on portions of PII, with the indexing tag, the electronic healthcare data is substantially de-identified because it contains no PII and the anonymous linking code which is based on portions of PII replaced by the indexing tag.

Then, in step 622, the healthcare data is compared to other healthcare data, and if the healthcare data is related to the same person, then the two sets of healthcare data are linked to or associated with each other. In the processor 210, the patient linkage module 218 compares the received electronic healthcare data to the electronic healthcare data stored in the storage device 208, and if the received electronic healthcare data and the stored electronic healthcare data are related to the same person, then the received electronic healthcare data is linked to the stored electronic healthcare data. The patient linkage module 218 can link or associate electronic healthcare data by assigning each the same appended anonymous linking code, the same indexing tag, or a combination of the aforementioned. The patient linkage module 218 can also use PII that is not subject to HIPAA to ensure that the received electronic healthcare data is linked to the correct corresponding stored electronic healthcare data. For example, since the zip code may not be subject to HIPAA, the zip code of the received electronic healthcare data can be used to verify that it has been linked to the correct corresponding electronic healthcare data stored in the storage device 208 by comparing the zip codes associated with each. Also, the received electronic healthcare data can be flagged to indicate that the storage device 208 already has electronic healthcare data associated with the anonymous linking code and/or the indexing tag. Thus, by linking or associating received electronic healthcare data with stored electronic healthcare data, the data warehouse 200 collects and accumulates healthcare data associated with one person.

In one exemplary embodiment, the data warehouse 200 maintains a master table stored in the storage device 208 which contains all previously received anonymous linking codes and their associated PII that is not subject to HIPAA. Each combination of anonymous linking codes and associated PII not subject to HIPAA is tabulated by the indexing tag. The patient linkage module 218 then compares the received anonymous linking code and associated PII not subject to HIPAA to previously received anonymous linking codes and their associated PII not subject to HIPAA. If the received anonymous linking code and associated PII not subject to HIPAA match a previously received anonymous linking code and associated PII not subject to HIPAA, then both are considered related to the same person. Thus, the received anonymous linking code and associated PII not subject to HIPAA are assigned the indexing tag of the matching previously received anonymous linking code and associated PII not subject to HIPAA. If the received anonymous linking code and associated PII not subject to HIPAA do not correspond to any previously received, then they are considered not related to the same person. Therefore, the received anonymous linking code and PII not subject to HIPAA are added to the master table and assigned a previously unused indexing tag.

Finally, in step 624, a report 212 is outputted. In the processor 210, the report creation module 220 outputs a report 212, step 520. The report 212 provides statistical analysis of stored healthcare data, demographic analysis of stored healthcare data, and other similar outputs. The contents of the report 212 can be customized to the requirements of the user. For example, the report 212 can include how often a certain medical procedure was completed in a certain city, the demographic data associated with prescriptions of a certain class of drugs, and other similar data. The report 212 can be, but not limited to, a paper report, electronic data, a data feed, a program, or any other suitable output. The report creation module 220 can create a report 212 with a predetermined form and format.

The report 212 provided is available in near real-time because the report 212 can be provided shortly after the healthcare data 112 is entered into the system 10. By providing near real-time reports, the data warehouse 200 can provide detection and tracking of specific diseases and syndromes by analyzing records for that specific malady. The report 212 can also be used for detection and geo-spatial tracking of a new infectious disease by searching the stored healthcare data for the occurrence of the new infectious disease and how frequently the new disease occurs in different geographical areas and then reporting the results of the search. The data warehouse 200 can also track other events, such as bioterrorism events that impact the healthcare system in a way similar to infectious diseases.

Figure 4:
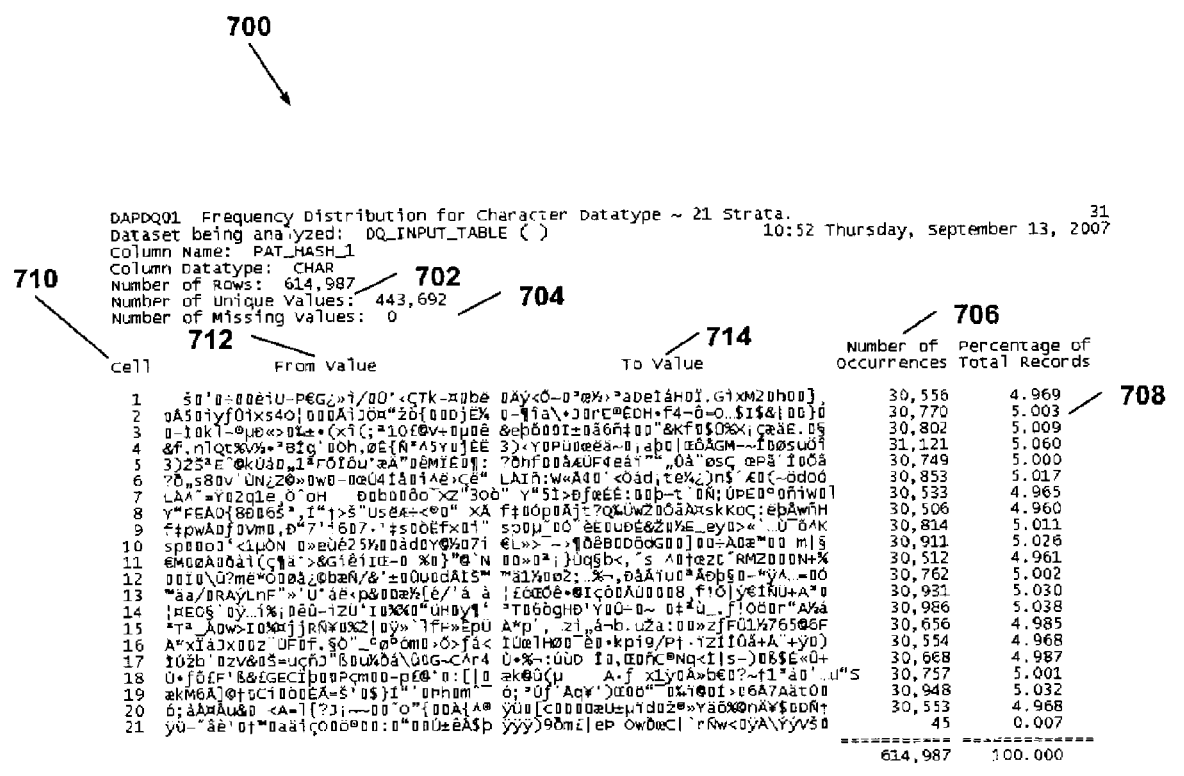

Referring to FIG. 4, an example report 700 is shown. In the example report 700 shown, the example report 700 provides statistical data concerning the number of unique anonymous linking codes. The report 700 states that, in an analysis of 614,987 records (provided under "Number of Rows" 702), 443,692 unique anonymous linking codes were found, as indicated next to "Number of Unique Values" 704. The report 700 also provides the "Number of Occurrences" 706 which indicates how frequently a particular anonymous linking code appears in the 614,897 records analyzed. Under "Percentage of Total Records" 708, the report provides what percentage of the 614,897 records analyzed had a particular anonymous linking code. To keep the report 700 brief, the report 700 divides the anonymous linking codes into 21 groups or "Cells" 710 that are defined between a "From Value" 712 and a "To Value" 714. The anonymous linking codes in the example report 700 are presented in their hashed and coded form.

Additionally, as the system 10 processes healthcare data 112 or the method is performed, data required by the system 10 or while performing the method is stored in the database 108 or in the memory of the processor 110. Data that is stored includes, for example, the predetermined portions of PII, algorithms to implement the present invention, the first hash function, the second hash function, the key, and other data that is not immediately needed.

The processes performed by any one or more modules can be accomplished by a predefined algorithm, tables, combinations of algorithms and tables, or other similar methods. For example, the operations of the extraction and encryption module 116, the concatenation module 118, the first hash function module 120, the second hash function module 122, the encryption for transmission module 126, the data transmission module 128, the data reception module 214, the decryption module 216, the patient linkage module 218, and the report creation module 220 can each be performed by a predefined algorithm. In particular, for instance, the first and second hash function modules 120 and 122 to form the anonymous linking code can be implemented as separate or combined algorithms. In other embodiments, the operations of the extraction and encryption module 116, the encryption for transmission module 126, the decryption module 216, and the patient linkage module 218 can be completed by use of tables.

To describe one implementation of the system 10 and the method, the following exemplary embodiment is provided and described in detail. However, the invention is not intended to be limited to the following exemplary embodiment. In the exemplary embodiment, the system 10 and method are applied to a data supplier of prescription claims, such as a pharmacist or a doctor. Because it supplies data, the data supplier is also the data source 100. A local computer work station is provided as the data source 100 and includes the user interface 102, the processor 110, and the database 108.

The work station also includes a computer keyboard to function as the input device 106, a monitor to function as the display 104, a conventional central processing unit and associated memory to function as the processor 110, and a hard drive to store the programming and electronic healthcare data 112. The hard drive also contains a computer database program to function as the database 108.

Figure 5:
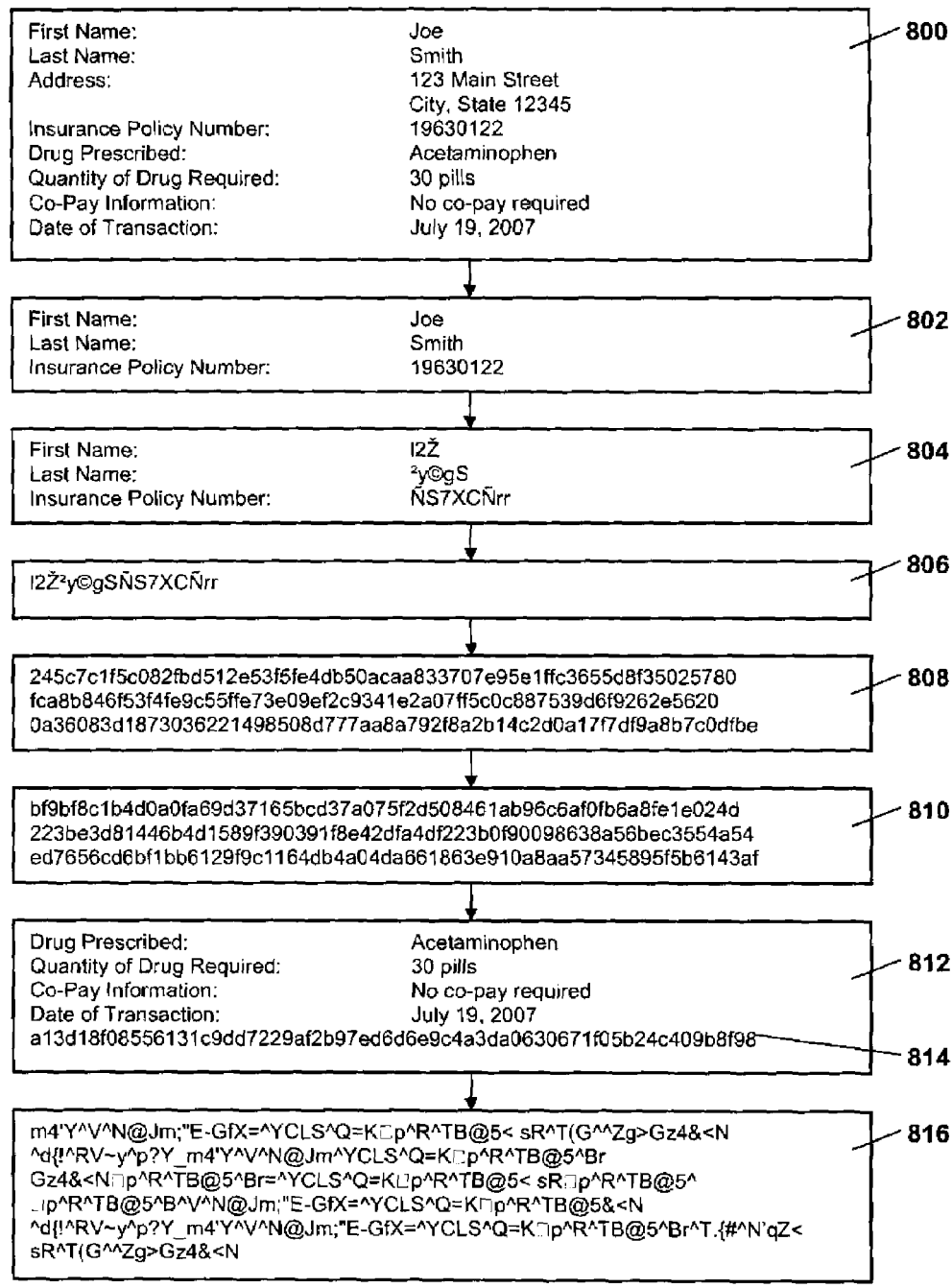
FIG. 5 is a flow diagram showing how healthcare data is manipulated by the system illustrated in FIG. 1.

Referring to FIG. 5, a flow diagram illustrating how healthcare data 112 is processed by the system 10 and the method is shown. In the exemplary embodiment, as shown in block 800, the healthcare data 112 is a drug prescription claim which includes discrete informational elements such as the patient's name, address, insurance policy number, the drug prescribed, the quantity of the drug required, co-pay information, and date of the transaction. The drug prescription claim is considered PHI since it is healthcare data with PII, such as the patient's name, address, and insurance policy number. The patient provides or the pharmacist collects elements of the healthcare data 112. The elements of the healthcare data 112 are asked for in specific fields shown on the display 104. The data 112 is entered into the fields through the keyboard functioning as the input device 106. Because the system 10 and method can be implemented with industry-specific formatting for data 112, a specific format such as NCPDP 5.1 can determine the order of the fields and the order in which data 112 is entered into the system. The data 112 is then electronically stored in the hard drive of the work station. The hard drive has an electronic database 108 which stores and tracks electronic healthcare data 112. The electronic database 108 can store the data 112 in a specific format such as NCPDP 5.1 on the hard drive.

In accordance with step 602, the data retrieval module 114 retrieves healthcare data 112 from the hard drive, as described in step 414 of FIG. 2. Since the healthcare data 112 is in a known predetermined order such as NCPDP 5.1, the system 10 is able to reorder the elements so that, for example, the patient's first name, the patient's last name, and the patient's insurance policy number are the first three elements followed by non-protected healthcare data such as the drug prescribed, the quantity of the drug required, co-pay information, and date of the transaction. The programming stores the reordered data in an extract file which is then stored on the hard drive in a predetermined subdirectory.

The programming next reads predetermined portions of PII such as the patient's name, address, and insurance policy number into the memory of the processor 110. In accordance with step 604 of the method, the extraction and encryption module 116 of the programming then uses the predetermined parts of the PII to create the anonymous linking code, as described in step 416 of FIG. 2. In the exemplary embodiment, as shown in block 802 of FIG. 5, the programming uses the first name, the last name, and the insurance policy number. First, the programming reads from the electronic healthcare data and stores in memory the data in the "first name" field, the "last name" field, and the "insurance policy number" field. After reading the data in the "first name" field, the "last name" field, and the "insurance policy number" field, the programming nulls the data in the "first name" field, the "last name" field, and the "insurance policy number" field. Also, the programming removes spaces and other non-alphabetic characters from the first name data, the last name data, and the insurance policy number data store in memory.

The extraction and encryption module 116 of the programming then encrypts the data. As shown in block 804, the system 10 performs a character substitution on the data in block 802. To complete character substitution, each character of the last name, the first name, and the insurance policy number is substituted with another character in accordance with a predetermined character substitution scheme stored in the database 108, the processor 112, the storage device 208, the processor 212, or any combination of the aforementioned. For instance, as shown, the first name "Joe" is encrypted as "|2Ž".

Then, at step 606, the concatenation module 118 of the programming concatenates or sequences in a predetermined order the parts of PII being used to create the anonymous linking code, as described in step 418 of FIG. 2. For example, the concatenation module 118 orders the data in block 804 such that the encrypted first name is followed immediately by the encrypted last name and then immediately by the encrypted insurance policy number, as shown in block 806 of FIG. 5.

To execute step 608 of the method, the concatenated name and insurance policy number are then inserted in a first hash function by the first hash function module 120 of the programming, as described in step 420 of FIG. 2. If the first hash function is an SHA-256, the hash function converts the last name, the first name, and the insurance policy number into a 64 digit hexadecimal number using 64 characters from the set including {0, 1, . . . 9, A, B, . . . F}. Also, since the hash function is keyed, the first hash function module 120 of the programming appends a key to the end of the output. The key is fixed and remains the same from one application to the next. In the exemplary embodiment, the key is a fixed character string of 64 characters chosen independently from the other characters in the key and randomly selected from the set of printable, non-blank ASCII characters from 0x21 ("!") to 0x7E ("~"). To maintain the secrecy of the key in the exemplary embodiment, the key is not stored as a single character string. Instead, in the exemplary embodiment, whenever the key is required, the software assembles the key from its constituent parts which are embedded in coded portions of the programming. In block 808 of FIG. 5, an example output of the first hash function based on the data in block 806 is shown.

Next, in accordance with step 610 of the method, the output of the first hash function with the appended key is inputted into a second hash function by the second hash function 122 module of the programming, as described in step 422 of FIG. 2. In the exemplary embodiment, the second hash function is substantially similar to the first hash function and converts the 64 hexadecimal number (the first hash function output) and appended character string of 64 characters (the key) into another 64 digit hexadecimal number. The key is appended to the output of the second hash function to create the anonymous linking code. An example output of the second hash function based on the first hash function output in block 808 is shown in block 810 of FIG. 5.

In step 612 of the method, the anonymous linking code 814 is appended to the end of the extract file and remaining PII is removed from the extract file. The de-identification module 124 of the programming appends the anonymous linking code 814 and removes any remaining PII subject to HIPAA from the extract file, as described in step 424 of FIG. 2. In FIG. 5, block 812 depicts the anonymous linking code 814 appended to the end of non-protected healthcare data. Also, because all PII subject to HIPAA has been removed, the extract file has several nulled bits that represented the removed PII, and the extract file now contains fields with no data interspersed among the data elements. Thus, a new file is created from the extract file, and the new file has no nulled bits and no fields without data. The programming sequentially examines each data field of the extract file and copies only fields with data into the new file. Thus, when compared to the extract file, the new file shifts data elements by skipping data fields without data. Therefore, as shown in block 812 of FIG. 5, because the data fields and data for the "first name," the "last name," and the "insurance policy number" have been removed, the programming shifts the remaining data elements, such as the "drug prescribed," the "quantity of drug required," "co-pay information," and "date of transaction" to make up for the bytes removed when PII not subject to HIPAA was removed from the extract file.

The resulting extract file with the anonymous linking code 814 appended at the end, PII subject to HIPAA removed, and the data shifted to compensate for the missing PII forms a modified extract file, substantially similar to the data shown in block 812 of FIG. 5. The modified extract file is stored in another predetermined subdirectory on the hard drive. The encryption for transmission module 126 of the programming then encrypts the modified extract file for transmission in accordance with step 614 of the method and as described in step 426 of FIG. 2. In the exemplary embodiment, the modified extract file is encrypted by using ICE. Block 816 of FIG. 5 depicts the result of encrypting the data in block 812 using ICE. Next, as described in step 428 of FIG. 2, the data transmission module 128 of the programming transmits the encrypted modified extract file on the secure data pathway 300, step 616 of the method. In the exemplary embodiment, after being encrypted by ICE, the modified extract file is transmitted by secure FTP to the data warehouse 200.

In the exemplary embodiment, the data warehouse 200 includes a local computer work station which includes the user interface 202, the processor 210, and the storage device 208. Software is provided on the computer work station to implement the system 10 and the method. The software includes programming that embodies the data reception module 214, the decryption module 216, the patient linkage module 218, and the report creation module 220.

The work station also includes a computer keyboard to function as the input device 206, a monitor to function as the display 204, a conventional central processing unit and associated memory to function as the processor 210, and a hard drive to store the programming and electronic data. The hard drive also contains a computer database program to function as the storage device 208.

As described in step 514 of FIG. 2, the data reception module 214 of the programming receives the encrypted modified extract file from the secure data pathway 300, step 618 of the method. In the exemplary embodiment, the data reception module 214 receives the encrypted modified extract file from secure FTP. The encrypted modified extract file received by the data reception module 214 is the output from the encryption for transmission module 126. In the exemplary embodiment, this corresponds to the data shown in block 816 of FIG. 5. Then, the decryption module 216 of the programming decrypts the encrypted modified extract file, step 620 of the method. In the exemplary embodiment, the decryption module 216 removes the ICE encryption completed by the encryption for transmission module 126, step 516 of FIG. 2. Thus, the decrypted modified extract file is now back to data shown in block 812 of FIG. 5. The modified extract file can also be sent to the data source 100, and the data source 100 can decrypt the anonymous linking code 814 by using the first and second hash functions to recover the predetermined portions of the PII.

To execute step 622 of the method, the patient linkage module 218 of the programming links the received modified extract file to stored modified extract files, as described in step 518 of FIG. 2. In the exemplary embodiment the storage device 208 contains a master table which tracks all previously encountered anonymous linking codes and their associated PII not subject to HIPAA. Each unique combination of anonymous linking code and associated PII not subject to HIPAA is given an indexing tag so that each patient has a unique indexing tag.

The programming extracts the anonymous linking code 814 from the modified extract file of block 812 and compares the anonymous linking code 814 and PII elements not subject to HIPAA of the received modified extract file to the anonymous linking codes and associated PII not subject to HIPAA of previously encountered modified extract files tabulated on the master table. If the received anonymous linking code 814 and associated PII elements not subject to HIPAA match a previously encountered anonymous linking code and associated PII elements not subject to HIPAA, the received anonymous linking code 814 and associated PII elements not subject to HIPAA are assigned the indexing tag of the matching previously encountered anonymous linking code and associated PII elements not subject to HIPAA. Matching anonymous linking codes indicate that the corresponding modified extract files are for the same patient. Matching PII elements not subject to HIPAA verifies that the modified extract files are for the same patient.

However, if the received anonymous linking code 814 and PII elements not subject to HIPAA do not correspond to any previously encountered anonymous linking code and associated PII elements, then the received anonymous linking code 814 and associated PII elements not subject to HIPAA are inserted into the master table, and a previously unused indexing tag is assigned to the anonymous linking code 814 and associated PII elements not subject to HIPAA. The modified extract file is also stored at the data warehouse 200, and the transactions contained in the modified extract file are available for analysis and reporting. In the exemplary embodiment, prescription transactions with the same indexing tag are considered to belong to the same patient and can be analyzed and reported as such.

Using the anonymous linking code 814 allows healthcare data files to be correlated to the same patient without having to use information that identifies the patient, such as PII. Thus, the anonymous linking code 814 does not have to be reverted back to its constituent predetermined portions of PII to correlate healthcare data files to the same patient. Furthermore, the data warehouse 200 never has PII subject to HIPAA, but the data warehouse 200 can still correlate healthcare data files from different data sources 100 created at different time to the same patient.

As described in step 520 of FIG. 2, the report creation module 220 of the programming provides analysis and reports based on the stored data, step 624 of the method. In the exemplary embodiment, the report creation module 220 can report cost per patient of a particular prescribed drug, the total payments made on behalf of a particular patient, and other similar data. Also by using the indexing tag and/or the anonymous linking code, the report provided protects the identity of the patient. Thus, the system 10 and the method provide analysis and reports for a single patient without revealing the patient's identity in compliance with HIPAA requirements. In the exemplary embodiment of FIG. 5, an example report may include how often acetaminophen has been prescribed to the anonymous linking code 814 associated with Joe Smith.

The foregoing description and drawings should be considered as illustrative only of the principles of the invention. The invention may be configured in a variety of embodiments and is not intended to be limited by the particular embodiments described. Numerous applications of the invention will readily occur. Therefore, it is not desired to limit the invention to the specific examples disclosed or the exact operation shown and described. Rather, all suitable modifications and equivalents may be resorted to, falling within the scope of the invention.

What is claimed is:

1. A system for protecting and de-identifying healthcare data, the system comprising:
   one or more computers;
   a first set of non-transitory storage devices storing instructions that are operable, when executed by one or more computers, and causes the one or more computers to perform the steps of:
   retrieving healthcare data and personally identifiable information of a person;
   storing in a second set of non-transitory storage devices, the retrieved healthcare data and personally identifiable information for the person;
   identifying a portion of the stored personally identifiable information from the storage device;
   extracting the identified portion of the personally identifiable information from the storage device;
   encrypting the extracted portion of the personally identifiable information;
   inputting, into a keyed hash function, the encrypted portion of the personally identifiable information;
   generating, by the keyed hash function, a first output;
   inputting the generated first output to a second hash function;
   generating, by the second hash function, a second output;
   generating an anonymous linking code using the second output;
   storing the anonymous linking code in association with the healthcare data for the person.

2. The system of claim 1, wherein the portion of the personally identifying information comprises a predetermined set of one or more personal identifiers, and wherein there is a functional relationship between the generated anonymous linking code and the one or more personal identifiers included in the predetermined set.

3. The system of claim 1, further comprising:
   a second storage device that receives and store the healthcare data with the appended anonymous linking code; and
   a second processor in communication with the second database storage device.

4. The system of claim 3, wherein the second processor uses the appended anonymous linking code of the received healthcare data to link the received healthcare data with stored healthcare data with a corresponding appended anonymous linking code.

5. The system of claim 3, wherein the healthcare data with the appended anonymous linking code is received from a secure data pathway.

6. The system of claim 3, wherein the second processor outputs a report based on the stored healthcare data.

7. The system of claim 1, wherein the keyed hash function is a keyed SHA-256 hash function.

8. The system of claim 1, wherein the second hash function is a SHA-256 hash function.

9. A computer-implemented method for protecting and de-identifying healthcare data containing personally identifiable information, the method comprising:
   retrieving, by one or more computers, healthcare data and personally identifiable information of a person;
   storing, by the one or more computers, in a storage device, the retrieved healthcare data and personally identifiable information for the person;
   identifying, by the one or more computers, a portion of the stored personally identifiable information from the storage device;
   extracting, by the one or more computer processor, the identified a portion of the personally identifiable information from the storage device;
   encrypting, by the one or more computer processor, the extracted portion of the personally identifiable information;
   inputting, into a keyed hash function, the encrypted portion of the personally identifiable information;
   generating, by the keyed hash function, a first output;
   inputting, by the one or more computer processors, the generated first output to a second hash function;
   generating, by the second hash function, a second output;
   generating, an anonymous linking code using the second output;
   storing the anonymous linking code in association with the healthcare data for the person.

10. The method of claim 9, further comprising the step of transmitting the healthcare data with the appended anonymous linking code to a data warehouse.

11. The method of claim 10, wherein the portion of the personally identifying information comprises a predetermined set of one or more personal identifiers, and wherein there is a functional relationship between the generated anonymous linking code and the one or more personal identifiers included in the predetermined set.

12. The method of claim 9, further comprising the step of linking a first healthcare data file with a second healthcare data file by their respective appended anonymous linking codes,
   wherein the first and second data files are for a particular person, and
   wherein the first and second data files are from different sources or are created at different times.

13. The method of claim 9, wherein the keyed hash function is a keyed SHA-256 hash function.

14. The method of claim 9, wherein the second hash function is a SHA-256 hash function.

* * * * *